(12) United States Patent
Woodruff et al.

(10) Patent No.: US 11,413,132 B2
(45) Date of Patent: Aug. 16, 2022

(54) SYSTEMS AND METHODS FOR LIGAMENT GRAFT PREPARATION

(71) Applicant: Medos International Sarl, Le Locle (CH)

(72) Inventors: Scott A. Woodruff, Boston, MA (US); Mehmet Z. Sengun, Canton, MA (US); Brian D. Busconi, Hopkinton, MA (US); Dean C. Taylor, Durham, NC (US)

(73) Assignee: Medos International Sarl, Le Locle (CH)

( * ) Notice: Subject to any disclaimer, the term of this patent is extended or adjusted under 35 U.S.C. 154(b) by 534 days.

(21) Appl. No.: 16/444,809

(22) Filed: Jun. 18, 2019

(65) Prior Publication Data

US 2019/0328505 A1 Oct. 31, 2019

Related U.S. Application Data

(63) Continuation of application No. 15/994,000, filed on May 31, 2018, now Pat. No. 10,357,355, which is a
(Continued)

(51) Int. Cl.
*A61F 2/08* (2006.01)
*A61B 17/06* (2006.01)
(Continued)

(52) U.S. Cl.
CPC .............. *A61F 2/08* (2013.01); *A61F 2/0811* (2013.01); *A61B 17/06061* (2013.01);
(Continued)

(58) Field of Classification Search
CPC .. A61F 2/08; A61F 2/0811; A61F 2002/0852; A61F 2002/087;
(Continued)

(56) References Cited

U.S. PATENT DOCUMENTS

| 4,143,426 A | 3/1979 | Hall et al. |
| 4,469,101 A | 9/1984 | Coleman et al. |

(Continued)

FOREIGN PATENT DOCUMENTS

| DE | 202014007804 U1 | 10/2014 |
| EP | 2777613 A1 | 9/2014 |

(Continued)

OTHER PUBLICATIONS

European Search Report for Application No. 16205252.6 dated May 12, 2017.
(Continued)

*Primary Examiner* — Yashita Sharma

(57) ABSTRACT

Systems and methods for preparing a ligament graft for a ligament reconstruction procedure are provided. In general, the described techniques utilize a graft preparation system having a holder and a delivery suture assembly removably coupled thereto. The delivery suture assembly can include a spine coupled with an anchor suture configured to form a self-tightening knot used to position the assembly around a graft and a plurality of suture windings configured to be affixed to the graft when the assembly is deployed. The assembly is delivered to the graft using the holder and the sutures can be affixed to the graft without penetrating therethrough. The spine helps to evenly distribute the load among the windings compressing the graft which are thus capable of withstanding increased loads. Thus, an improved, simplified, and time- and labor-saving approach to preparing ligament grafts is provided.

7 Claims, 24 Drawing Sheets

Related U.S. Application Data continuation of application No. 14/327,358, filed on Jul. 9, 2014, now Pat. No. 9,993,332.

(51) Int. Cl.
  *A61B 17/04* (2006.01)
  *A61B 17/11* (2006.01)

(52) U.S. Cl.
  CPC ... *A61B 17/1146* (2013.01); *A61B 2017/0477* (2013.01); *A61B 2017/06171* (2013.01); *A61B 2017/06185* (2013.01); *A61F 2002/087* (2013.01); *A61F 2002/0852* (2013.01); *A61F 2220/0075* (2013.01); *A61F 2240/00* (2013.01); *A61F 2240/001* (2013.01)

(58) Field of Classification Search
  CPC .......... A61F 2220/0075; A61F 2240/00; A61F 2240/001; A61F 2002/0882; A61B 17/06061; A61B 17/1146; A61B 2017/0477; A61B 2017/06171; A61B 2017/06185; A61B 5/4533; A61B 17/06166
  See application file for complete search history.

(56) References Cited

U.S. PATENT DOCUMENTS

| | | | |
|---|---|---|---|
| 4,759,765 | A | 7/1988 | Van Kampen |
| 4,946,377 | A | 8/1990 | Kovach |
| 4,979,956 | A | 12/1990 | Silvestrini |
| 5,061,283 | A | 10/1991 | Silvestrini |
| 5,144,961 | A | 9/1992 | Chen et al. |
| 5,281,422 | A | 1/1994 | Badylak et al. |
| 5,284,485 | A | 2/1994 | Kammerer et al. |
| 5,306,301 | A | 4/1994 | Graf et al. |
| 5,372,821 | A | 12/1994 | Badylak et al. |
| 5,456,721 | A | 10/1995 | Legrand |
| 5,527,341 | A | 6/1996 | Gogolewski et al. |
| 5,540,703 | A | 7/1996 | Barker, Jr. et al. |
| 5,573,784 | A | 11/1996 | Badylak et al. |
| 5,628,756 | A | 5/1997 | Barker, Jr. et al. |
| 5,645,588 | A | 7/1997 | Graf et al. |
| 5,769,862 | A | 6/1998 | Kammerer et al. |
| 5,800,543 | A | 9/1998 | McLeod et al. |
| 6,056,752 | A | 5/2000 | Roger |
| 6,080,184 | A | 6/2000 | Peters et al. |
| 6,083,244 | A | 7/2000 | Lubbers et al. |
| 6,102,947 | A | 8/2000 | Gordon |
| 6,106,556 | A | 8/2000 | Demopulos et al. |
| 6,143,029 | A | 11/2000 | Rippstein |
| 6,203,572 | B1 | 3/2001 | Johnson et al. |
| 6,260,696 | B1 | 7/2001 | Braginsky et al. |
| 6,296,659 | B1 | 10/2001 | Foerster |
| 6,322,571 | B1 | 11/2001 | Adams |
| 6,342,060 | B1 | 1/2002 | Adams |
| 6,602,290 | B2 | 8/2003 | Esnouf et al. |
| 6,821,286 | B1 | 11/2004 | Carranza et al. |
| 7,371,253 | B2 | 5/2008 | Leung et al. |
| 7,465,308 | B2 | 12/2008 | Sikora et al. |
| 7,892,256 | B2 | 2/2011 | Grafton et al. |
| 8,202,318 | B2 | 6/2012 | Willobee |
| 8,231,654 | B2 | 7/2012 | Kaiser et al. |
| 8,298,247 | B2 | 10/2012 | Sterrett et al. |
| 8,298,284 | B2 | 10/2012 | Cassani |
| 8,403,947 | B2 | 3/2013 | Ochiai |
| 8,439,936 | B2 | 5/2013 | McClellan |
| 8,460,350 | B2 | 6/2013 | Albertorio et al. |
| 8,500,809 | B2 | 8/2013 | Saliman |
| 8,562,645 | B2 | 10/2013 | Stone et al. |
| 8,574,296 | B2 | 11/2013 | Missos |
| 8,591,544 | B2 | 11/2013 | Jolly et al. |
| 8,591,578 | B2 | 11/2013 | Albertorio et al. |
| 8,652,172 | B2 | 2/2014 | Denham et al. |
| 8,663,324 | B2 | 3/2014 | Schmieding et al. |
| 8,690,960 | B2 | 4/2014 | Hotter et al. |
| 8,888,848 | B2 | 11/2014 | Saliman et al. |
| 9,011,533 | B2 | 4/2015 | Gadikota et al. |
| 9,060,854 | B2 | 6/2015 | Altman et al. |
| 9,101,462 | B2 | 8/2015 | Miller |
| 10,357,355 | B2 | 7/2019 | Woodruff et al. |
| 2003/0050668 | A1 | 3/2003 | Lee |
| 2003/0130735 | A1 | 7/2003 | Rogalski |
| 2007/0123984 | A1 | 5/2007 | Hodorek |
| 2007/0239275 | A1 | 10/2007 | Willobee |
| 2007/0250163 | A1 | 10/2007 | Cassani |
| 2007/0288023 | A1 | 12/2007 | Pellegrino et al. |
| 2007/0288040 | A1 | 12/2007 | Ferree |
| 2008/0188936 | A1 | 8/2008 | Ball et al. |
| 2009/0018655 | A1 | 1/2009 | Brunelle et al. |
| 2009/0105754 | A1 | 4/2009 | Sethi |
| 2009/0228021 | A1 | 9/2009 | Leung |
| 2009/0306688 | A1 | 12/2009 | Patel et al. |
| 2009/0318958 | A1 | 12/2009 | Ochiai |
| 2010/0145367 | A1 | 6/2010 | Ratcliffe |
| 2010/0179591 | A1 | 7/2010 | Saltzman et al. |
| 2010/0222792 | A1 | 9/2010 | Barnes et al. |
| 2010/0249802 | A1 | 9/2010 | May et al. |
| 2011/0015735 | A1 | 1/2011 | Persson |
| 2011/0160749 | A1 | 6/2011 | Gordon et al. |
| 2011/0238179 | A1 | 9/2011 | Laurencin et al. |
| 2012/0046746 | A1 | 2/2012 | Konicek |
| 2012/0239145 | A1 | 9/2012 | Peterson et al. |
| 2012/0253465 | A1 | 10/2012 | Missos |
| 2013/0013065 | A1 | 1/2013 | Bills |
| 2013/0023907 | A1 | 1/2013 | Sterrett et al. |
| 2013/0023927 | A1 | 1/2013 | Cassani |
| 2013/0116730 | A1 | 5/2013 | Denham et al. |
| 2013/0123937 | A1 | 5/2013 | Jamiolkowski et al. |
| 2013/0274879 | A1 | 10/2013 | Champagne et al. |
| 2013/0296936 | A1 | 11/2013 | Burkhart |
| 2014/0024885 | A1 | 1/2014 | Sudekum |
| 2014/0074239 | A1 | 3/2014 | Albertorio et al. |
| 2014/0163586 | A1 | 6/2014 | Holt |
| 2014/0243891 | A1 | 8/2014 | Schmieding et al. |
| 2014/0257346 | A1 | 9/2014 | Sengun et al. |
| 2014/0257384 | A1 | 9/2014 | Dreyfuss et al. |
| 2014/0277448 | A1 | 9/2014 | Guerra et al. |
| 2014/0350675 | A1 | 11/2014 | Hackney et al. |
| 2015/0025552 | A1 | 1/2015 | Stoll |
| 2015/0039030 | A1 | 2/2015 | Saliman et al. |
| 2015/0051700 | A1 | 2/2015 | Collette |
| 2015/0057750 | A1 | 2/2015 | Timmerman |
| 2015/0066059 | A1 | 3/2015 | Sinnott et al. |
| 2015/0073441 | A1 | 3/2015 | Fallin et al. |
| 2015/0134060 | A1 | 5/2015 | Chudik |
| 2015/0201924 | A1 | 7/2015 | Gordon et al. |
| 2015/0201925 | A1 | 7/2015 | Benavitz |
| 2015/0216542 | A1 | 8/2015 | Libby et al. |
| 2015/0238318 | A1 | 8/2015 | McCullen |
| 2015/0245831 | A1 | 9/2015 | Sullivan |
| 2015/0245841 | A1 | 9/2015 | Linder et al. |
| 2017/0172725 | A1 | 6/2017 | Gustafson |
| 2019/0231516 | A1 | 8/2019 | Gustafson |

FOREIGN PATENT DOCUMENTS

| | | | |
|---|---|---|---|
| EP | 2923672 | A1 | 9/2015 |
| JP | 2001506902 | A | 5/2001 |
| JP | 2011522590 | A | 8/2011 |
| JP | 2011522590 | A1 | 8/2011 |
| WO | 9827894 | A1 | 7/1998 |

OTHER PUBLICATIONS

European Search Report for Application No. 15176016.2, dated Nov. 9, 2015. (7 pages).

U.S. Appl. No. 14/977,882, filed Dec. 22, 2015, Graft Preparation System.

U.S. Appl. No. 14/327,358, filed Jul. 9, 2014, Systems and Methods for Ligament Graft Preparation.

(56) References Cited

OTHER PUBLICATIONS

U.S. Appl. No. 15/994,000, May 31, 2018, Systems and Methods for Ligament Graft Preparation.
U.S. Appl. No. 16/380,530, filed Oct. 4, 2019, Graft Preparation System.

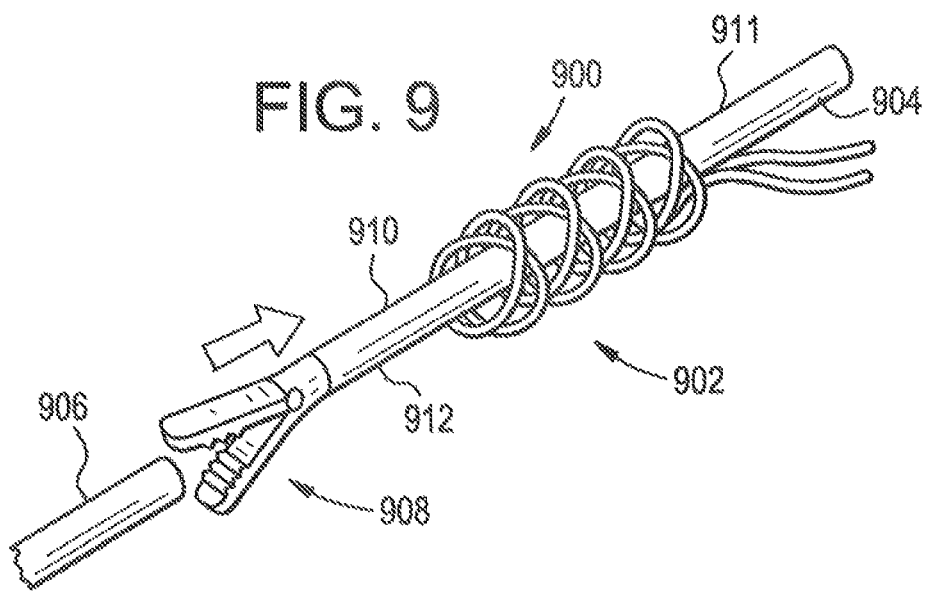
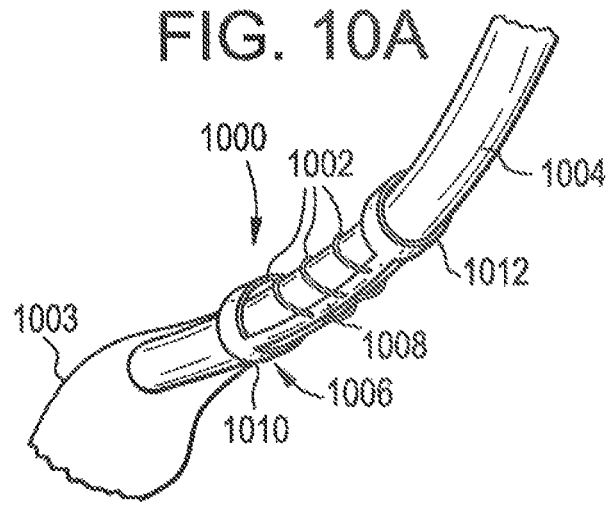
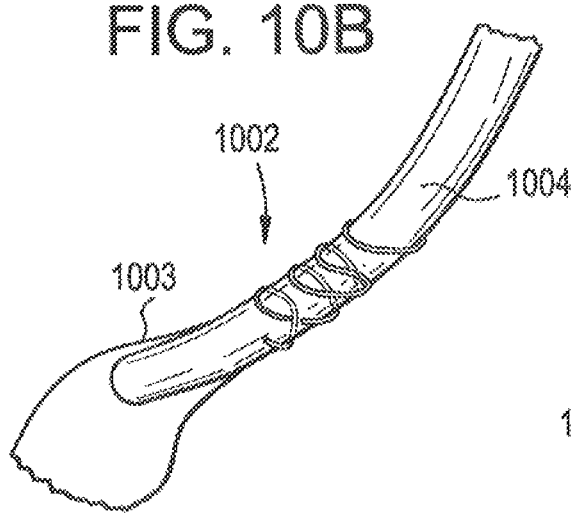
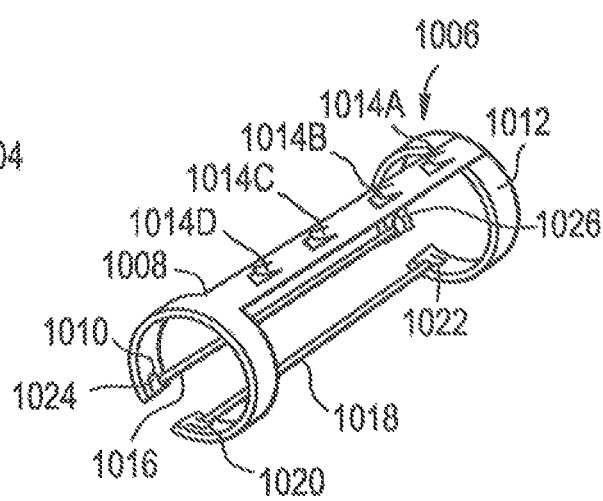

SYSTEMS AND METHODS FOR LIGAMENT GRAFT PREPARATION

CROSS REFERENCE TO RELATED APPLICATIONS

The present application is a continuation of U.S. patent application Ser. No. 15/994,000 entitled "Systems and Methods for Ligament Graft Preparation" filed May 31, 2018, which is a continuation of U.S. patent application Ser. No. 14/327,358 (now U.S. Pat. No. 9,993,332) filed Jul. 9, 2014 and entitled "Systems and Methods for Ligament Graft Preparation" which are hereby incorporated by reference in its entirety.

FIELD

The present invention relates to systems and methods for preparing ligament grafts.

BACKGROUND

A ligament is a piece of fibrous tissue which connects one bone to another within the body. Ligaments are frequently damaged (e.g., detached, torn or ruptured) as the result of injury or accident. A damaged ligament can impede proper motion of a joint and cause significant pain. A damaged ligament can be replaced or repaired using various procedures, a choice of which can depend on a particular ligament to be restored and on the extent of the damage. When ligaments are damaged, surgical reconstruction can be necessary, as the ligaments may not regenerate on their own.

An example of a ligament that is frequently damaged as a result of injury, overexertion, aging and/or accident is the anterior cruciate ligament (ACL) that extends between a top of the tibia and a bottom of the femur. A damaged ACL can cause instability of the knee joint, arthritis, and substantial pain.

ACL repair typically includes the use of a ligament graft replacement procedure which usually involves drilling a bone tunnel through the tibia and up into the femur. Then a ligament graft, which may be an artificial ligament or harvested graft, such as a tendon, is passed through a tibial portion of the tunnel (sometimes referred to as "the tibial tunnel") across the interior of the joint, and up into a femoral portion of a tunnel (sometimes referred to as "the femoral tunnel"). One end of the ligament graft can then be secured in the femoral tunnel and another end of the graft is secured in the tibial tunnel, at the sites where the natural ligament attaches.

Another ligament that is often damaged and may need to be replaced is a posterior cruciate ligament (PCL).

A common ligament reconstruction procedure involves using an autograft, which is a patient's own tendon that would replace the damaged natural ligament. The autograft is often a hamstring tendon, though other tendons can be used (e.g., a patellar tendon). The ligament graft can also be obtained from a donor ("allograft").

Ligament augmentation and replacement procedures typically require preparation of a harvested ligament graft using various techniques to secure the graft for passing through the drilled tunnels and to strengthen the graft prior to fixation. The preparation may involve cleaning and measuring the graft, and then affixing sutures to free ends thereof. The thus prepared graft can be tensioned prior to being inserted into the femoral and tibial tunnels.

FIG. 1 illustrates an example of a graft 100 prepared using a conventional whip-stitching (simple or locking) technique. A needle (not shown) or other suture passing instrument can be used to pass a suture 102 through the graft 100 to create stitches some of which are labeled as 102A and 102B in FIG. 1. The whip-stitching can have certain drawbacks. For example, it may cause trauma to the graft and undesirable excessive elongation of the graft when a load is applied thereto. This can compromise the quality of the graft 100 and create a risk of complications during the ligament reconstruction procedure.

Other existing graft preparation techniques include, for example, baseball stitching, roman sandal suture techniques, krackow and Prusik knots.

The conventional approaches to graft preparation, such as the whip-stitching technique described above, can be labor- and time-consuming and may take up a large portion of time during a reconstruction surgery. Placing a suture on the graft can be cumbersome and, when a graft is prepared using such techniques, the entire reconstruction procedure may be put on hold, which can contribute to increased costs of the surgery. In addition, the surgeon or other medical personnel sewing the stitches bears a risk of a needle-stick injury which can lead to potential infections.

Accordingly, there is a need for improved techniques for preparing grafts.

SUMMARY

A graft preparation system is provided that in some embodiments can comprise a spine having first and second ends, a plurality of windings formed from a first suture and spaced longitudinally along the spine, each winding being coupled to the spine by passing the first suture through attachment elements longitudinally spaced along the spine, and a second, anchor suture configured to position the spine and the plurality of windings coupled thereto around a graft, the anchor suture being coupled to the spine by passing through at least one of the attachment elements adjacent to the first end of the spine.

The graft preparation system can vary in any number of ways. For example, at least one of the attachment elements can comprise an eyelet formed in the spine. The eyelet may be formed integrally with the spine. The graft preparation system may further comprise an elongate holder having a first surface and a second surface and it may be configured to receive the graft adjacent the second surface thereof. The spine can be removably positioned along the first surface of the elongate holder. In some embodiments, at least one element selected from the spine, the plurality of windings, and the anchor suture can be removably coupled with the holder.

The elongate holder can have any number of variations. For example, the elongate holder can have a configuration that can be changed to separate the spine from the elongate holder. In some embodiments, the elongate holder can be substantially cylindrical in shape and the second surface can be an inner surface. In other embodiments, the elongate holder can comprise a substantially rectangular element and the second surface can be an inner surface. The holder can have any suitable size and shape.

In some embodiments, windings from the plurality of windings can form a criss-crossing pattern along a surface of the elongate holder. In some embodiments, windings from the plurality of windings include first and second tails extending from the second end of the spine opposite to the first end of spine being coupled to the anchor suture.

The anchor suture can vary in any number of ways. For example, the anchor suture can be configured to form a collapsible loop surrounding the holder and can be selectively removable therefrom. In some embodiments, the anchor suture may be configured to form a snare comprising a self-tightening knot. The anchor suture can be formed integrally with the spine. In some embodiments, the anchor suture can be configured to penetrate through the graft.

In another aspect, a method of preparing a graft for a surgical procedure is provided that in some embodiments comprises positioning a graft preparation system around a portion of the graft, the graft preparation system comprising a holder and a delivery suture assembly comprising a spine positioned along a first surface of the holder, a plurality of windings that are spaced longitudinally along the spine such that the windings are coupled to the spine, and a second, anchor suture coupled to the spine. The method can also comprise separating the holder from the portion of the graft such that the delivery suture assembly remains positioned around the portion of the graft and the holder is removed, manipulating the anchor suture to affix the delivery suture assembly adjacent a first end of the portion of the graft without penetrating the graft, and, after the delivery suture assembly is affixed around the first end of the portion of the graft, manipulating at least one suture tail of the windings to secure the plurality of windings around the portion of the graft without penetrating the graft such that the windings are spaced apart along a length of the portion of the graft.

The method can vary in any number of ways. For example, following the positioning of the graft preparation system, the windings and the anchor suture can form loose loops around the portion of the graft. Manipulating the anchor suture can comprise pulling a tail of the anchor suture in a first direction, and manipulating the at least one suture tail of the windings can comprise pulling first and second tails of the at least one suture tail in an opposite, second direction to tighten the loops upon the graft. The anchor suture can be secured to the portion of the graft with a self-locking snare.

In another aspect, a method of preparing a graft for a surgical procedure is provided that in some embodiments comprises positioning a delivery suture assembly around a portion of the graft, the delivery suture assembly comprising a spine, a plurality of windings that are spaced longitudinally along the spine such that the windings are coupled to the spine, and a second, anchor suture coupled to the spine. The method can also comprise pulling a tail end of the anchor suture in a first direction to affix the delivery suture assembly adjacent a first end of the portion of the graft without penetrating the graft; and after the delivery suture assembly is affixed around the first end of the portion of the graft, pulling at least one suture tail of the windings to secure the plurality of windings around the portion of the graft without penetrating the graft such that the windings are spaced apart along a length of the portion of the graft.

The method can vary in any number of ways. For example, the delivery suture assembly can be positioned around the portion of the graft using a holder member having the delivery suture assembly removably associated therewith. The method can further comprise separating the delivery suture assembly positioned around the portion of the graft from the holder member such that the delivery suture assembly remains positioned around the portion of the graft and the holder member is removed. In some embodiments, separating the delivery suture assembly from the holder member may comprise changing a configuration of the holder member. The anchor suture can be secured to the portion of the graft with a self-locking snare.

In yet another aspect, a graft preparation assembly is provided that in some embodiments may comprise a spine having first and second ends and a plurality of windings formed from a first suture and spaced longitudinally along the spine, each winding being coupled to the spine by passing the first suture through attachment elements associated with the spine. The spine and the plurality of windings can be configured to receive a graft such that the windings are positioned around the graft. The plurality of windings may be associated with the spine by being longitudinally spaced along the spine. The graft preparation assembly may vary in a number of ways. For example, the graft preparation assembly may further include an anchoring element, which may be a separate suture or other element, or may be an extension of the spine. In some embodiments, the first suture may also be an extension of the spine.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 9 is a schematic illustration of an embodiment where a delivery suture assembly in accordance with some embodiments is provided to a graft without employing a holder;

FIGS. 10A-10C are schematic illustrations of employing a graft preparation system including a holder having an alternative configuration, in accordance with some embodiments;

DETAILED DESCRIPTION

Figure 1:
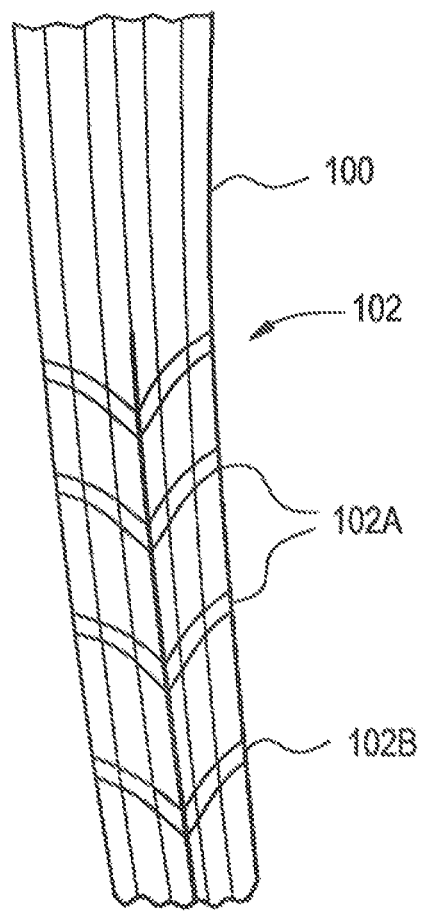
FIG. 1 (Prior Art) is a schematic illustration of a graft prepared using whip-stitching.

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to systems and methods for preparing ligament grafts for ligament reconstruction, or augmentation, surgeries. In some embodiments, the graft preparation system can include a holder and a delivery suture assembly comprising a spine, and an anchor suture and a plurality of suture windings coupled to the spine. The graft preparation system can be made such that it is ready to be deployed, which can greatly reduce the time required to affix sutures to the graft.

The holder can be used to deliver the delivery suture assembly to the graft, which can then be separated from the holder and affixed to the graft using a few steps. The anchor suture can include a pre-assembled self-tightening knot and can be used to lock a position of the windings around a graft. The spine having the windings coupled thereto helps to evenly distribute the load among the windings when they are deployed. In this way, the windings can be used to compress the graft more evenly, without strangulating it, and the suture can withstand increased loads. As a result, the strength of fixation of a delivery suture assembly to the graft can be improved.

Accordingly, the systems and methods described herein may have a number of advantages over existing techniques for preparing ligament grafts. In particular, the entire graft preparation procedure can be straightforward and requires a surgeon to take only a few quick steps to affix the delivery suture assembly to the graft. A need for whip-stitching or any other technique requiring penetrating the graft may be avoided. As a result, a risk of causing trauma to the graft can be reduced and a time required to prepare the graft can be significantly reduced, which can facilitate the surgery and mitigate inconvenience to the patient. Because a pre-assembled construct is utilized, the reproducibility of the procedure is improved. Thus, the described graft preparation procedure is simplified and is less labor-intensive, which improves efficiency of the ligament reconstruction procedure, and mitigates risks posed by conventional time-consuming and less reliable graft preparation techniques. In addition, the described techniques can help to save operating room costs.

The described techniques can be used in conjunction with a variety of ligament grafts, including hamstring ligament grafts, in a variety of different surgical contexts regardless of the type of ligament graft being used in a particular surgical procedure. The systems and methods described herein can be utilized in connection with preparing graft ligaments for repairing or replacing ligaments in a variety of joints, but can in some embodiments have particular utility in cruciate ligament reconstruction procedures. In some embodiments, the systems and methods described herein can be utilized for preparing ligament grafts for reconstruction procedures such as, for example, the cruciate ligaments of the knee.

Figure 2:
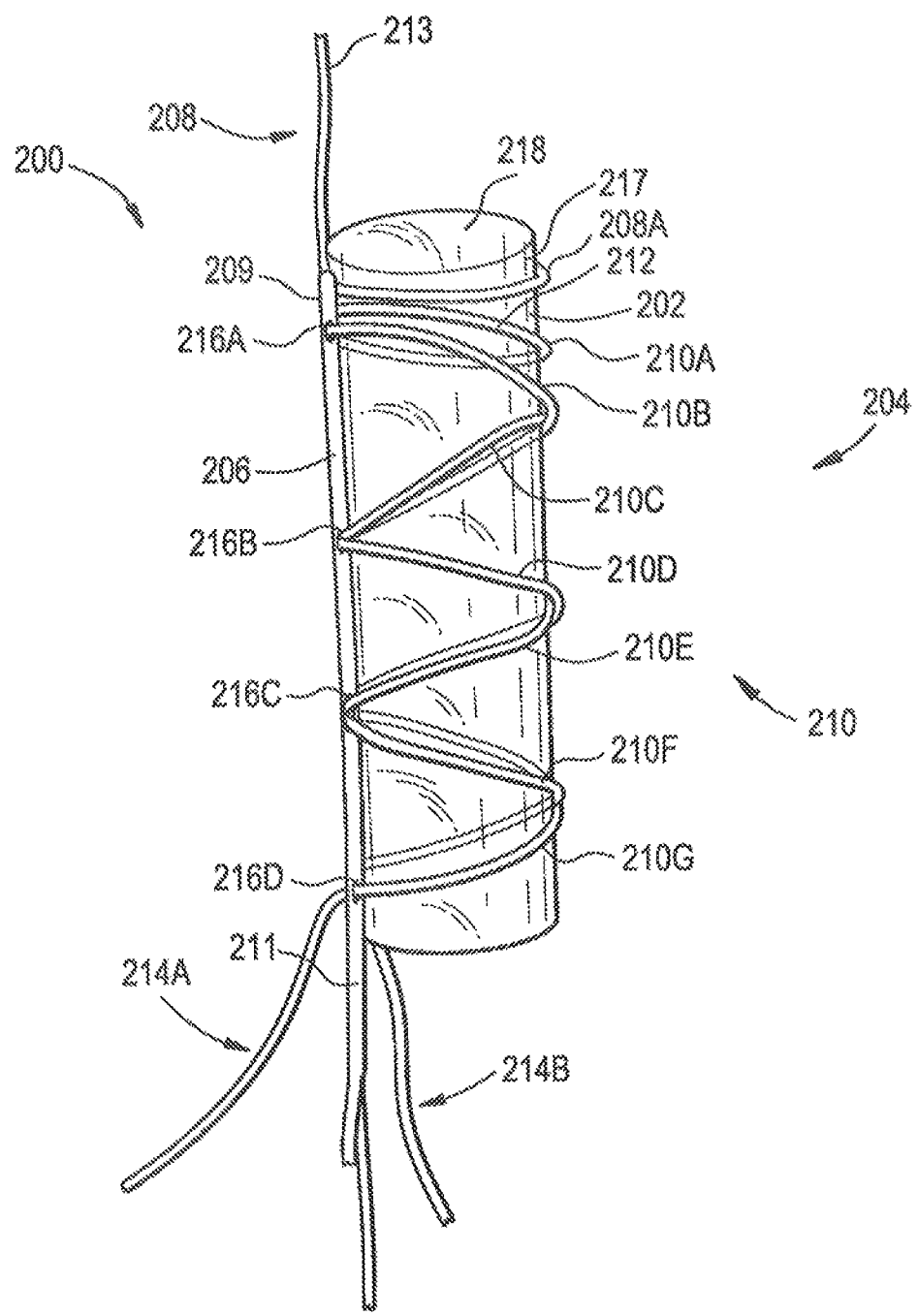
FIG. 2 is a schematic illustration of a graft preparation system in accordance with some embodiments.

FIG. 2 shows a graft preparation system 200 in accordance with some embodiments. The graft preparation system 200 can be pre-assembled and can be efficiently utilized by a medical professional to deliver sutures to a graft during a ligament reconstruction procedure without penetrating through the graft.

The graft preparation system 200 can include a holder 202 removably carrying a delivery suture assembly 204. The delivery suture assembly 204 can include a spine 206, an anchor suture 208 and a plurality of windings 210, individually labeled as windings 210A-210G which are formed from a suture 212 having tails 214A and 214B. As illustrated, the anchor suture 208 and the windings 210 are coupled to the spine 206.

The holder 202 can have any suitable configuration that allows separating the delivery suture assembly 204 therefrom. In FIG. 2, the holder 202 is an elongate member having a first, outer surface 217, and a second, inner surface 218. The outer surface 217 can have the delivery suture assembly 204 associated therewith, and the inner surface 218 can be configured to receive a graft when the graft preparation system 200 is deployed to affix sutures 208, 212 to the graft.

In the example of FIG. 2, the elongate holder 202 is substantially cylindrical in shape. As used herein, "substantially cylindrical" means generally having the shape of a cylinder, either with or without a contour, which can be an open or closed cylinder. However, it should be appreciated that the substantially cylindrical holder 202 is shown by way of example only, and a holder carrying a delivery suture assembly in accordance with embodiments described herein can have any suitable configuration. For example, the holder can be a foldable and/or collapsible element, for example, a card shown in FIGS. 8A-8C, a wire cage or other suitable element. The holder can also be a component having at an end thereof a feature configured to be attached to a ligament graft. An example of such a holder can be a surgical grasper (FIG. 9). When the ligament graft is attached to the holder, the delivery suture assembly may be manipulated to slide off or otherwise separate from the holder to thereby be positioned over the graft.

As another example, in some embodiments and discussed below with respect to FIGS. 10A-10C, the holder may comprise an implantable element which may be an integral part of the delivery suture assembly such that the entire holder or one or more of its parts are not separated from the delivery suture assembly upon positioning of the assembly around the graft. For example, the holder can form the spine such that the spine is a part of the holder. In such cases, the spine can be at least partially formed from a plastic or other suitable material that is sufficiently rigid such that the spine itself can be used to deliver the delivery suture assembly coupled therewith to the graft. Additionally or alternatively, the holder can be configured such that its surface can carry the spine and the anchor suture only, or the spine, the anchor suture positioned at one end of the spine and the winding positioned at the other, opposite end of the spine. Such configurations may allow the holder to have only minimal contact with the delivery suture assembly, such that the size and surface area of the holder can be reduced.

In some embodiments, the delivery suture assembly can be deployed to a graft without the use of a removable holder. In such embodiments, the windings of the delivery suture assembly (with or without the anchor suture) may be configured so as to maintain a configuration that can allow them to be positioned over the graft. For example, the windings can have "open" configuration such that the delivery suture assembly can be easily applied to the graft to subsequently be secured thereon. Various techniques may be used to prepare the delivery suture assembly such that it can be delivered to a graft without a separate holder. For example, prior to being deployed, the delivery suture assembly can be reinforced using a suitable material such as, e.g., biocompatible coatings, wax of any suitable type, surgical glue or any other suitable material that can be used to stiffen the suture windings such that they maintain a configuration suitable for receiving a graft through the windings.

Referring back to FIG. 2, the configuration of the holder can be changeable such that a user (e.g., a surgeon or other medical professional) can manipulate the holder to separate it from the delivery suture assembly removably associated therewith. Furthermore, the holder 202 can have suitable structural features that enhance its function of delivering the delivery suture assembly to a graft. For example, the outer surface of the holder 202 can have one or more features that facilitate coupling of the anchor suture and/or the spine thereto. In one embodiment, the holder can have a feature that allows maintaining the anchor suture at an end of the holder.

As shown in FIG. 2, the spine 206 can be positioned along a length of the holder 202, such as along the outer surface 217 thereof. In the example of FIG. 2, the outer surface 217 can be an outer wall which circumscribes an arc in a range of about 180° to 360°. A person skilled in the art will appreciate that the spine 206 can have any suitable length. For example, in the embodiment illustrated in FIG. 2, the spine 206 extends beyond the holder 202; however, the spine 206 can have the same length as the holder 202 or it can be shorter than a longitudinal length or other dimension of the holder 202. The length of the spine 206 can be selected such that the spine 206 can support a desired number of suture windings while adequately distributing load among the windings and eventually along a portion of the graft.

The spine 206 can have associated therewith attachment elements 216A-216D, which, in the example of FIG. 2, are longitudinally spaced along the spine 206 between first and second ends 209, 211 thereof. The attachment elements 216A-216D can be eyelets, which can be formed integrally with the spine 206—for example, from the same suture that is used to form the spine 206, as discussed in more detail below. As used herein, an "eyelet" can be an opening formed by a loop of the suture, or an opening formed through the suture by penetrating therethrough. In some embodiments, the spine can be formed using crocheting or other technique thereby the spine can have eyelet formed therein. The spine can be formed using a suitable suture material. In some embodiments, however, the spine may be formed from different types of material(s), including materials that are typically not used for sutures.

The opening can have any suitable size and shape, and can be formed in any suitable manner. It should be appreciated that other types of attachment elements can be associated with the spine 206, as embodiments are not limited in this respect. The attachment elements 216A-216D can all be of the same type (e.g., eyelets). Alternatively, in some embodiments, one or more of the attachment elements 216A-216D can be of a type that is different from that of other attachment elements. Furthermore, four attachment elements 216A-216D are shown by way of example only, as any suitable number of attachment elements can be used. In addition, the suture 212 and the anchor suture 208 can simply be passed through the spine 206, in an embodiment of a spine that does not include attachment elements.

As further shown in FIG. 2, both the anchor suture 208 and the suture 212 can be coupled to the spine 206 via the attachment element 216A that is adjacent the first end 209 of the spine. The attachment element 216A can be, for example, an eyelet. The eyelet can be formed integrally with the spine 206, or in some other suitable manner.

The anchor suture 208, which is used to anchor the spine 206 to the graft at a desired location, can be coupled to the spine 206 by passing it through an eyelet or in any other manner. In one embodiment, the anchor suture 208 can be secured adjacent the first end 209 of the spine 206, which is at a location that will be spaced away from a terminal end of a graft.

The anchor suture used to position and affix the suture windings around the graft in accordance with the described embodiments may be of any suitable type. For example, in some embodiments, rather than using a separate suture as the anchor suture, the anchor suture may be an extension of the spine. In such embodiments, the anchor suture may be trimmed to a suitable length after it is used to position the delivery suture assembly around the graft. The extension of the spine may be a single strand or, in some embodiments, it may be bifurcated into two stands or separated into more than two strands beyond the first end 209 of the spine. The anchor suture that is an extension of the spine may be formed integrally with the spine (and the suture or other element forming the spine can be, in some cases, separated into two or more strands that can serve as the anchor suture) or it may be a separate suture nonremovably coupled with the spine.

The anchor suture 208 can be configured to form a collapsible loop, or snare, 208A that surrounds the holder 202 prior to deployment of the delivery suture assembly 204. The loop 208A can be any form of a self-tightening knot and it can be formed in any suitable manner. When the delivery suture assembly 204 is deployed, the loop 208A can be removed from the holder 202, and the holder can be removed as well. The loop 208A and the anchor suture 208 can then be used to affix, or anchor, the spine 206 to a ligament graft. A tail 213 of the anchor suture 208 can be used to cause the loop 208A to collapse to thereby affix the anchor suture 208 to the graft.

It should be appreciated that the described techniques are not limited to any specific type of an anchor suture. Thus, in some embodiments, the anchor suture may be formed integrally with the spine—e.g., from the same suture or other element that is used to form the spine. Furthermore, in some cases, the anchor suture may not be used at all.

The windings 210A-210G formed from the suture 212 can be coupled to the spine 206 via the attachment elements 216A-216D longitudinally spaced along the spine 206. As shown in FIG. 2, the attachment element 216D is positioned at the second end 211 of the spine 206, opposite to the attachment element 216A positioned at the first end 209 of the spine 206. The second end 211 of the spine 206 will typically be positioned adjacent to a terminal end of a graft. As shown in FIG. 2, the attachment element 216A can be used to couple both the anchor suture 208 and the suture 212 to the spine 206. Each of the attachment elements 216A-216D can be an eyelet (e.g., an eyelet formed integrally with the spine 206) having one or more windings passing therethrough, or other type of an attachment element. For example, one or more separate elements can be used to couple the windings 210A-210G to the spine 206.

Regardless of the type of attachment elements utilized, the windings 210A-210G can be formed by passing portions of the suture 212 having respective tails 214A, 214B through the attachment elements (or through the spine in the absence of attachment element) and around the holder 202. As shown, the windings extend along a length of the holder 202 in a criss-cross like pattern. Each of the windings 210A-

210G can form a collapsible loop that is associated with the holder 202 prior to deployment of the delivery suture assembly 204. In some embodiments, the winding 210A positioned adjacent the end 209 of the spine 206 can act as a reinforcing winding additionally formed to improve the strength of attachment of the assembly to the graft.

It should be appreciated that the four attachment elements 216A-216D are shown in FIG. 2 as an example only, as any other number of attachment elements can be used for coupling any suitable number of windings to the spine. For example, in some embodiments, one or more of the attachment elements 216B-216D can include two attachment elements. In such an embodiment, one or more of the windings 210C-210G can be coupled to the spine 206 at respective close, but separate, locations along the spine 206. For example, the windings 210C and 210D can each be coupled to the spine 206 via a separate attachment element (e.g., an eyelet) located close to each other such that these attachment elements are shown as the single attachment element 216B in FIG. 2. The winding 210B can also be coupled to the spine 206 via an attachment element separate from the attachment element 216A. It should be appreciated, however, that, regardless of a number and type of attachment elements or locations at which the suture 212 forming the windings 210A-210G is passed through the spine, the windings 210A-210G can be coupled to the spine 206 such that they are approximately evenly distributed around the spine 206 and later around a graft.

Furthermore, in some embodiments, the windings 210 can be formed from the same suture or other element forming the spine. For example, the spine can be extended and bifurcated beyond the first end 209 thereof into two separate sutures, or strands, which can be used instead of the suture 212. As discussed above, in some embodiments, the anchor suture can also be formed as an extension of the spine. Thus, in some embodiments, both the windings and the anchor suture may be formed from the same element as the spine.

As shown in FIG. 2, the tails 214A and 214B of the suture 212 can extend from the second end 211 of the spine 206 opposite to the first end 209 thereof that is coupled to the anchor suture 208. The tails 214A and 214B can be manipulated when the delivery suture assembly 204 is deployed to affix the windings 210A-210G to the graft.

Figure 3A:
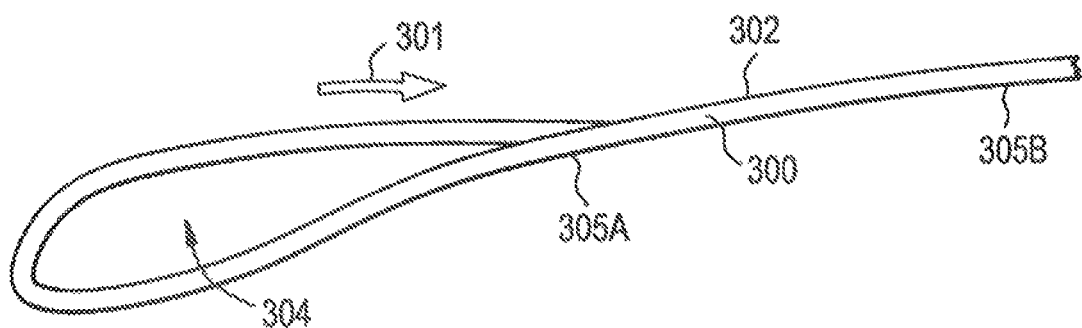
FIGS. 3A-3E are schematic illustrations of steps of making a graft preparation system in accordance with some embodiments.

FIGS. 3A-3E illustrate an exemplary embodiment of forming a delivery suture assembly (e.g., the delivery suture assembly 204 in FIG. 2). As shown in FIG. 3A, first, a suture 300 can be threaded into itself in a direction shown with an arrow 301 to thereby form a loop, or an eyelet, 304 and a spine 302 (e.g., the spine 206 of FIG. 2). The eyelet 304, shown as formed adjacent an end 305A of the spine 302, can serve as an attachment element, such as the attachment element 216A (FIG. 2). The suture 300 can be threaded into itself using any suitable technique known to those skilled in the art. A thickness of the suture 300 can be selected such that a portion of the suture can be threaded through another portion thereof without compromising the suture strength. For example, an end of the suture 300 can be guided (using a needle or other appropriate tool) in the direction 301 to leave a loop forming the eyelet 304 and to then pull the suture 300 back therethrough. A portion of the thus threaded suture 300 extending from the eyelet 304 can form the spine 302, which can have any suitable length. For example, in some embodiments, the spine 302 can have a length of at least about 30 millimeters (mm).

Figure 3B:
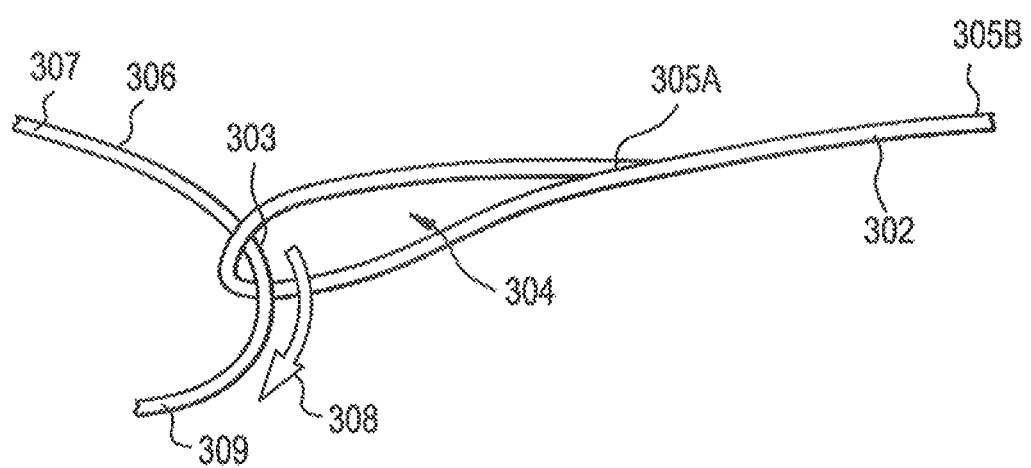

Next, as shown in FIG. 3B, a first suture 306 can be passed through the eyelet 304 in a direction shown by an arrow 308. This can be a suture (e.g., the anchor suture 208 of FIG. 2) configured to act as a counter-tensioning suture that anchors the delivery suture assembly to the graft. The first suture 306 can be positioned to extend away from both ends 305A and 305 B of the spine 302, as shown in FIG. 3B.

Figure 3C:
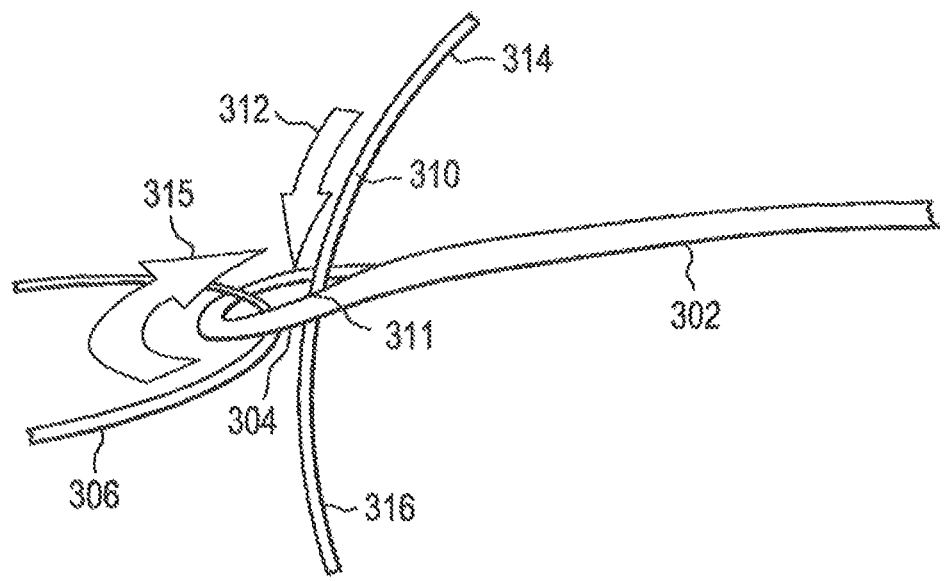

A second suture 310 can be passed through the eyelet 304 in a direction indicated by an arrow 312 in FIG. 3C. The suture 310 can be passed through the eyelet 304 such that a portion 311 of the suture 310 located approximately in the middle thereof is at least partially positioned within the eyelet 304. In this way, the suture 310 can be separated into two portions having respective free ends, or tails, 314 and 316 that can extend from the eyelet 304 as shown in FIG. 3C. The suture 310 can then be used to form windings, such as windings 210A-210G in FIG. 2, by passing tails 314 and 316 through the attachment elements and around a holder (not shown) in a criss-cross pattern to form the structure shown in FIG. 2 and as explained below. In this way, the eyelet 304 can be used to couple both sutures 306 and 310 to the spine 302. In one embodiment, a length of the suture 310 can be about 36 inches. However, it should be appreciated that the suture 310 can have any suitable length as embodiments are not limited in this respect.

The suture 306, which is also referred to herein as an anchor suture, can be manipulated to form a loop, or snare, comprising a self-tightening knot. The snare can be formed in any suitable manner and can be a collapsible loop that is capable of collapsing to form a knot when a tail of the loop is pulled. The snare can alternatively or additionally be a sliding knot, such as, for example, any type of knot well known to those skilled in the art. Any other sliding knots can be used as well. As schematically shown in FIG. 3C, the suture 306 can be passed through the eyelet 304 in a direction of an arrow 315 to form one or more loops (not shown) which can form the snare.

Sutures comprising any suitable materials can be used for the described graft preparation techniques. In some embodiments, the anchor suture 306, the suture 310 forming the windings, and the suture 300 forming the spine can comprise various surgical sutures, typically size 0 to size 5, such as Orthocord™ suture commercially available from DePuy Mitek, and Ethibond™ suture available from Ethicon. Orthocord™ suture is approximately fifty-five to sixty-five percent PDS™ polydioxanone, which is bioabsorbable, and the remaining percent ultra high molecular weight polyethylene, while Ethibond™ suture is primarily high strength polyester. The sutures can also comprise High-Molecular Weight (HMW) polyethylene sutures or HMW polyethylene sutures with a co-braid (e.g., monofilament polypropylene, nylon or other co-braid). In some embodiments, monofilament sutures such as, for example, Monocryl® available from Ethicon, may be utilized. As another example, an absorbable suture such as Vycryl® (a copolymer made from 90% glycolide and 10% L-lactide) also available from Ethicon may be used. The sutures 300, 306 and 310 can comprise any suitable amount and type of bioabsorbable material, which can depend on a particular surgical procedure and/or surgeon preferences.

The suture 300 can have a thickness and structure appropriate for a portion of it to be threaded through the suture itself. The sutures 300, 306 and 310 can comprise multiple threads that can be combined in a suitable manner to (e.g., using braiding, weaving, knitting, entangling and/or using any other technique) such that the suture has sufficient strength and a structural integrity of the suture is maintained even if it is penetrated.

In some embodiments, after one or both of the sutures 306 and 310 are passed through the eyelet 304, the eyelet 304 can be tightened around the suture(s) in a suitable manner. For example, suitable graft preparation or other type of equipment can be used such that appropriate components thereof are used to tighten the eyelet 304. It should be appreciated that embodiments are not limited to any specific technique that can be used to tighten the eyelet 304. Although not drawn to scale, FIGS. 3A-3E illustrate schematically that the eyelet 304 can be tightened—a loop forming the eyelet 304 in FIGS. 3A and 3B is wider than the eyelet 304 in FIGS. 3C-3E after the eyelet 304 has been tightened. It should be appreciated that, in some embodiments, the eyelet 304 can be tightened before either of the sutures 306 and 310 is passed therethrough.

Figure 3D:
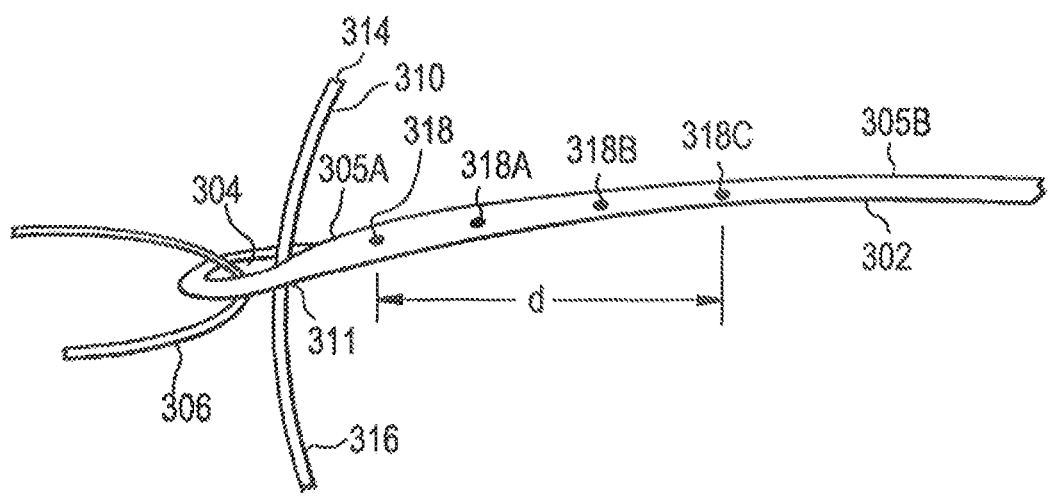

In some embodiments, markings 318-318D, shown in FIG. 3D can next be applied to the spine 302 formed from the suture 300 to visually identify sites at which the windings are to be coupled to the spine 302. The first marking 318 can be applied adjacent to the eyelet 304 at the end 305A of the spine 302. Alternatively, the marking 318 can be omitted. The markings 318A-318C, which identify locations at which the suture 310 is to be coupled (e.g., passed through or otherwise coupled) with the spine 302, can be longitudinally spaced along the spine 302 between the ends 305A and 305B thereof and can be formed at a suitable distance from the eyelet 304. In one embodiment, the markings 318A-318C can be equally or approximately equally spaced along a length of the spine 302. However, it should be appreciated that the markings 318A-318C can be spaced apart in any other manner, as the described techniques are not limited in this respect.

In one embodiment, a distance d between the marking 318 adjacent the eyelet 304 and the marking 318C that is formed adjacent the end 305B can be about 30 millimeters (mm), and all of the markings 318-318C can be spaced about 10 mm apart from each other. It should be appreciated, however, that the markings 318-318C that are spaced apart from each other at about equal distances are shown by way of example only, as the markings can be spaced apart from each other at any other distances, including different distances. The distances between the markings 318-318C can be selected based on a type of the graft, patient's characteristics, type of a reconstruction procedure, and any other factors. Furthermore, in some embodiments, the markings may be omitted altogether, or only some of them can be applied. Any others techniques may be used to identify sites of coupling the windings to the spine 302. As another variation, in some embodiments, the markings may be applied before one or both of the sutures 306 and 310 are coupled to the spine 302 via the eyelet 304.

Figure 3E:
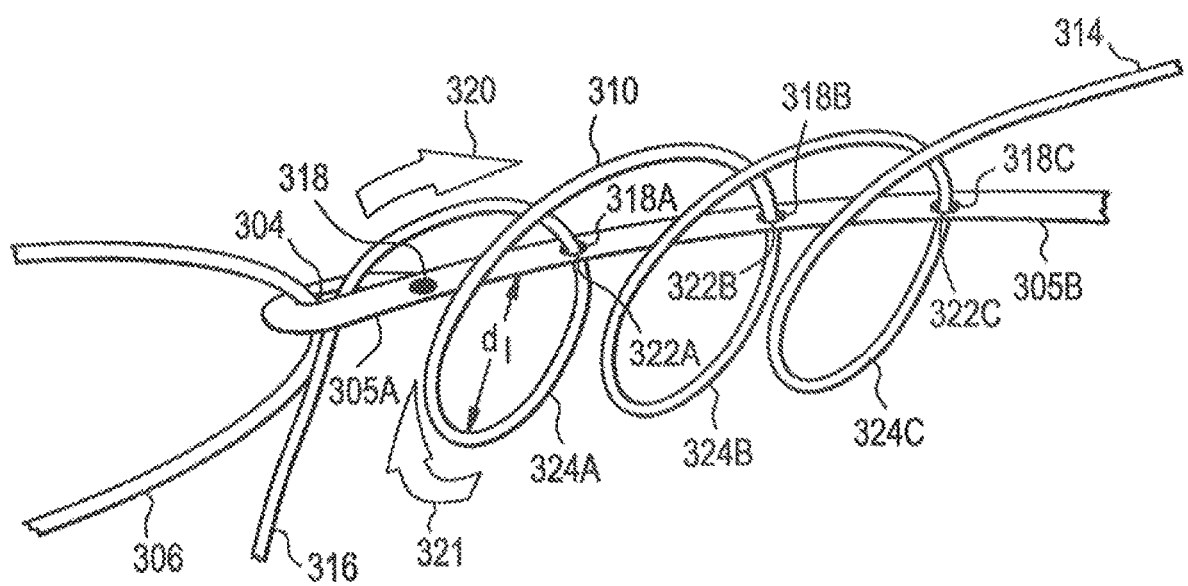

Regardless of the way in which locations for coupling windings to the spine 302 are identified along the length thereof, the suture 310 can then be manipulated such that one of its tails, for example, the tail 314, is passed through the spine 302 to create windings to be later affixed to the graft. For this purpose, a needle or other suture passing instrument (not shown) can be passed through the suture 310 and used to guide the tail 314 of the suture 310 to penetrate through the spine 302. As shown in FIG. 3E, the suture 310 can be threaded through the spine 302 by first passing, in the direction of an arrow 320—from the top to bottom, through the spine 302, at a location thereof identified by the marking 318A or in other manner. The needle can penetrate through the spine 302 via an eyelet 322A, which can be a portion of the spine or, in some embodiments, another attachment element using to couple a winding to the spine. After the suture 310 is pulled through the eyelet 322A, a portion of the suture 310 can be left loose such that a loop 324A is created. The length of this portion can be selected based on a desired size of a winding being created in this manner. FIG. 3E shows schematically a diameter l of the loop 324A, or a distance between the spine 302 and a widest portion of the loop 324A, which defines the diameter of the winding.

Next, the suture 310 can be passed around the spine 302 (as shown with an arrow 321) and, in a manner similar to the above, can be guided to pass through the spine 302 at the location of the marking 318B to thereby form another eyelet 322B. The suture 310 can be passed in the same way as it was passed through the eyelet 322A—from the top of the spine 302 to the bottom. However, it should be appreciated that the suture 310 can pass the spine 302 in the opposite direction as well.

After being passed through the eyelet 322B, a portion of the suture 310 can again be left loose to thereby form a loop 324B. A diameter of the loop 324B can be approximately the same as the diameter $d_1$ of the loop 324A. As a next step, the needle can be used to guide the suture 310 to penetrate through the spine 302 at the location identified by the marking 318C, to form an eyelet 322C. A portion of the tail 314 can extend from the loop 324C to be later used for tensioning the windings around the graft.

Although not shown in FIG. 3E, the suture 310 can next be passed once through the eyelet 304 (e.g., to form the winding 210A in FIG. 2) and the process above can be repeated for the portion of the suture 310 having the tail 316. For example, the needle or another suitable tool is used to guide the suture 310 by the tail 316 to be sequentially passed through the spine 302 through eyelets 322A, 322B and 322C, in the direction shown by the arrow 320—i.e., from the top to bottom, leaving loose portions of the suture 310 behind. Another set of loops similar to the loops 324A-324C can thus be formed from the suture 310. In this way, the windings, such as the windings 210A-210G of the delivery suture assembly 204 of FIG. 2, can be formed.

Regardless of the way in which the anchor suture and the plurality of suture windings coupled to the spine are formed, the resulting pre-assembled delivery suture assembly including the spine 302, the anchor suture 306 and the windings made as described above in connection with FIGS. 3A-3E can be coupled with a suitable component configured to provide the delivery suture assembly to a graft. The component can be a holder, such as the holder 202 shown in FIG. 2, although a component of any other type can be utilized additionally or alternatively. The delivery suture assembly can be coupled with the holder by passing the holder through the windings formed from the suture 310 and the loop or snare formed from the anchor suture 306 and positioning the spine 302 along a length of the holder.

It should be appreciated that the described techniques are not limited to any particular way in which the windings can be formed from a suture. For example, in some embodiments, rather than passing the suture 310 through the eyelet 304 (or securing it to an end of the spine in other manner) and then passing its portions having tails 314 and 316 through the spine 302 starting from the attachment element 322A, the suture 310 may not be passed through the eyelet 304 as the first step. Instead, as shown in FIGS. 3F-3M, a suture 310' can be passed through a spine 302' (or otherwise coupled thereto) starting from an opposite end 305B' towards an end 305A' thereof such that the suture 310' is passed through an eyelet 304' after one set of windings is created. Then, once it reaches the proximity of an eyelet 304', the suture 310' can be passed through the eyelet and another set of windings can be created by now passing the suture 310' through the spine 302' (or otherwise coupled thereto) in the opposite direction, from the end 305A' towards the end 305B', to thereby create another set of windings.

In the example illustrated in connection with FIGS. 3F-3M, the spine 302' has been formed (e.g., as shown above for the spine 302 or in any other manner) and the eyelet 304' has been formed (in this example, integrally with the spine). Also, a suture 306' serving as an anchor suture has been passed through the eyelet 304', which has been tightened around that suture, and two portions of the suture 306' may be held using a graft preparation instrument during the process of making a delivery suture assembly.

Figure 3F:
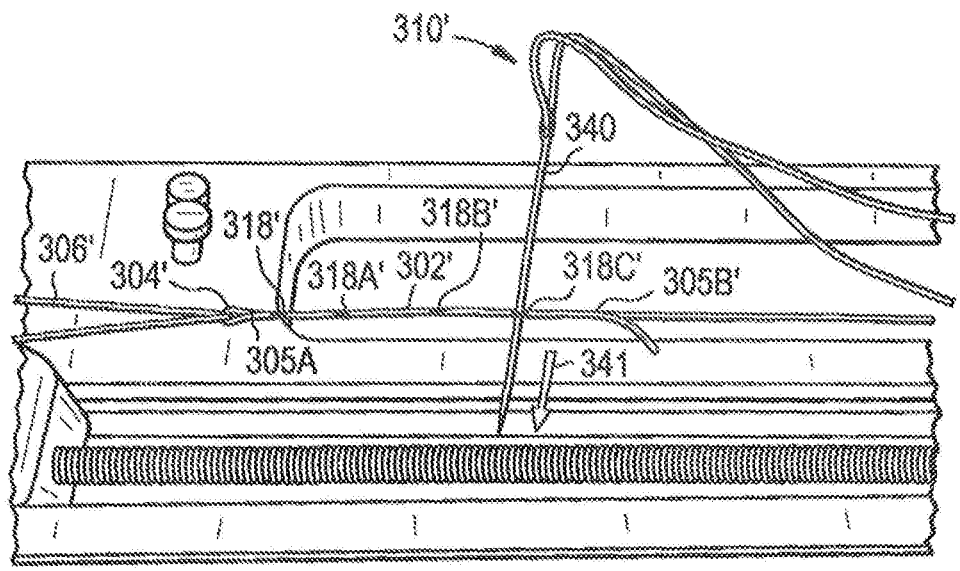
FIGS. 3F-3M are schematic illustrations of steps of making a graft preparation system in accordance with other embodiments.

As shown in FIG. 3F, using a needle 340 or other suture passing instrument, the suture 310' can be first passed through the spine 302' at a location of a marking 318C'. Similar to the manner of marking the spine 302 (as shown in FIGS. 3D and 3E), locations at which windings are to be coupled to the spine 302' may be identified by markings 318'-318C'. It should be appreciated, however, that the markings 318'-318C' are described by way of example only, as any other ways of identifying locations on the spine 302' to couple windings thereto can be used. Further, in some embodiments, the spine 302' can have attachment elements (e.g., eyelets, other types of openings, or any other attachment elements) which may additionally or alternatively be used to couple the windings to the spine. Thus, although only the markings 318'-318C' are shown in FIGS. 3F-3L for the sake of simplicity, it should be appreciated that the locations at which windings 324A'-324C' are coupled to the spine 302' may be identified in any other suitable manner, including without using any markings.

Figure 3G:
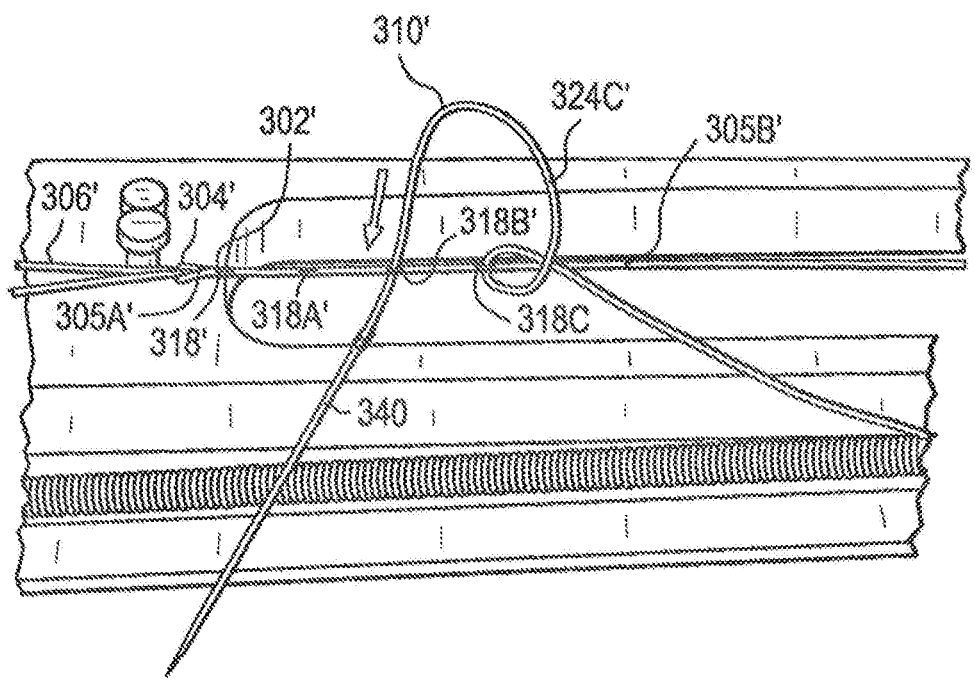
Figure 3H:
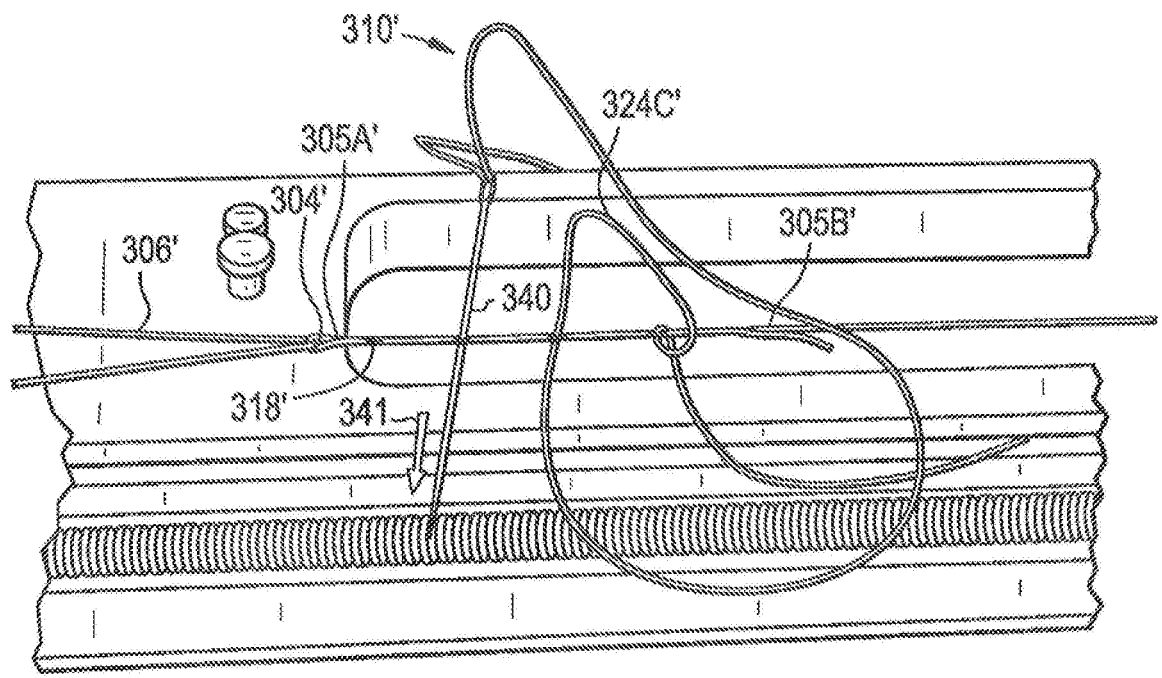
Figure 3I:
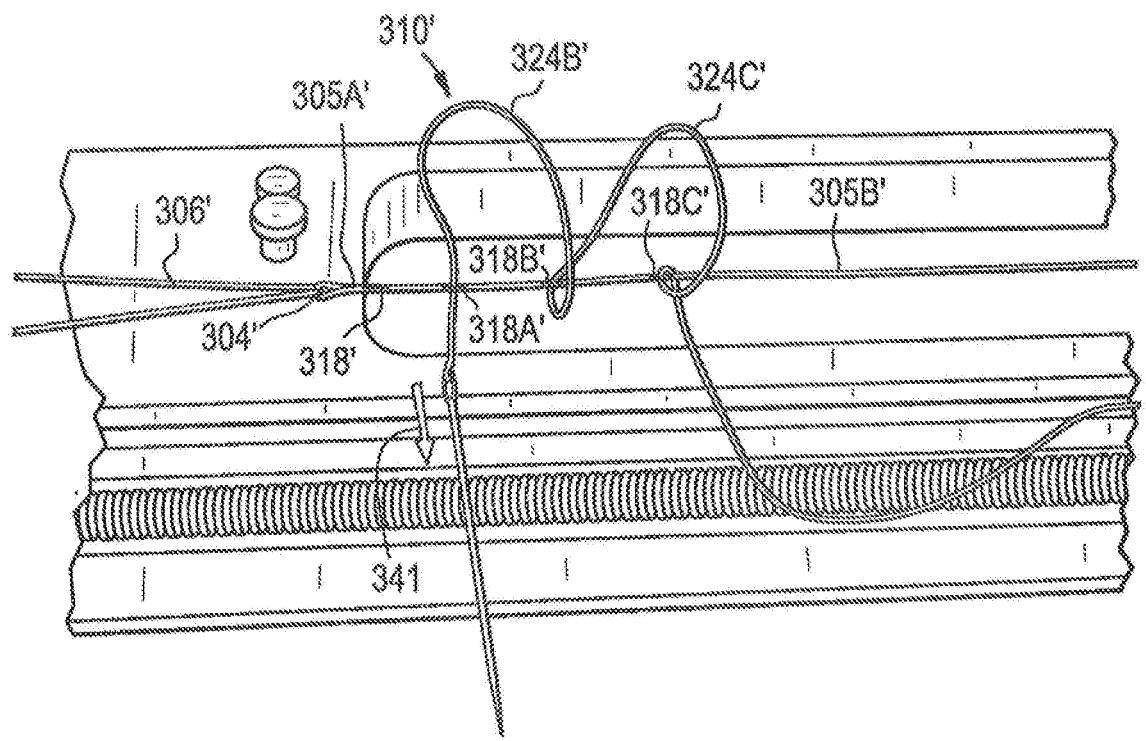

As shown in FIG. 3F, the needle 340 can be used to pass the suture 310' through the spine 302' from the top to the bottom, in a direction shown by an arrow 341 (other directions can be used instead), leaving a loose loop which can create the winding 324C' as shown in FIG. 3G. FIG. 3H illustrates that the suture 310' can then be passed through the spine 302' at a location identified by a marking 318B' which is closer to the end 305A' of the spine 302', again in the same direction—in this example, from the top to the bottom, leaving a loop thus forming the winding 324B' as shown in FIG. 3I. Next, the suture 310' can be passed through the spine 302' at a location identified by a marking 318A' to create a windings 324A' in the same manner as above.

Figure 3J:
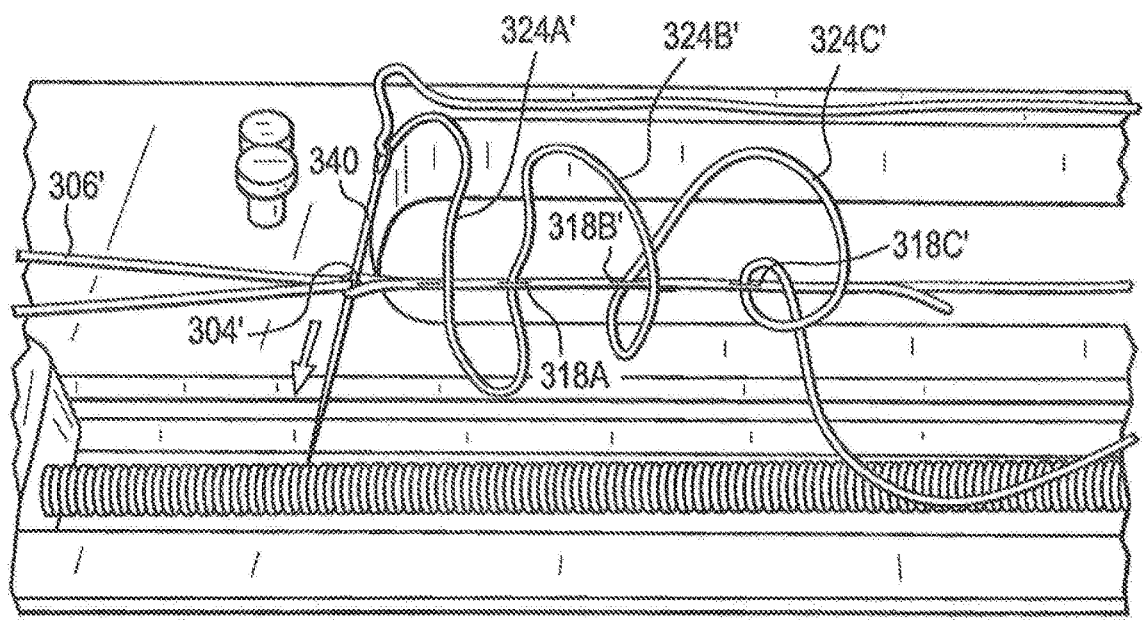
Figure 3K:
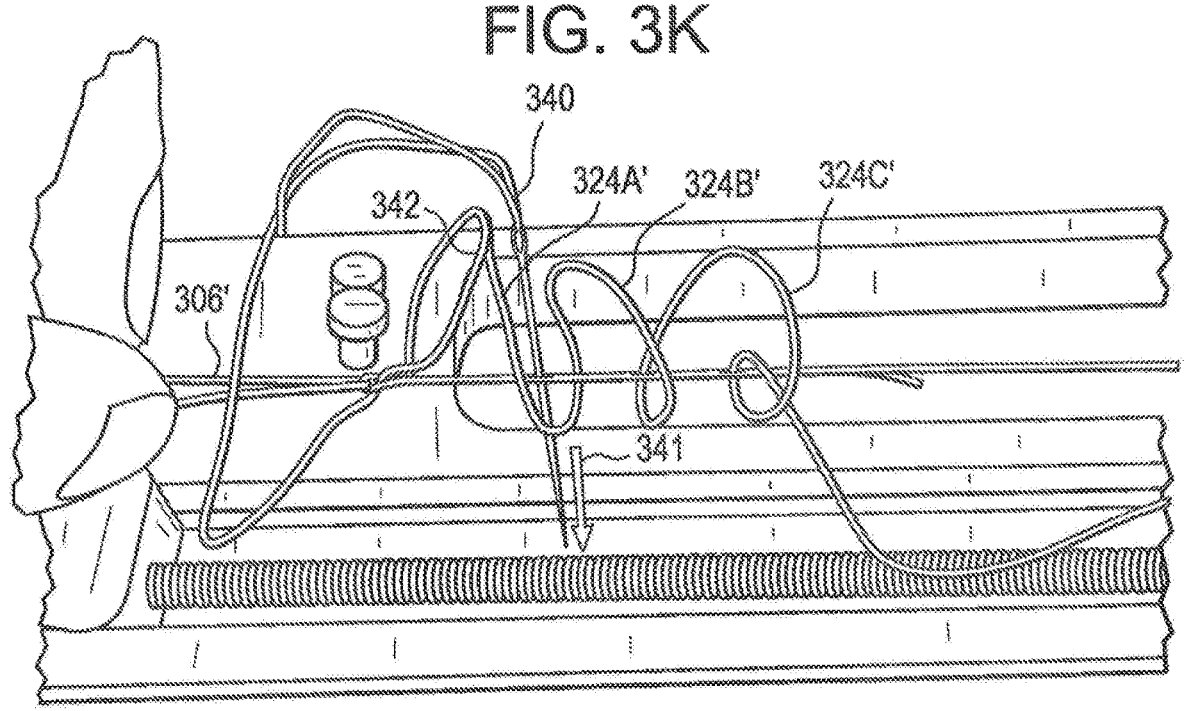
Figure 3L:
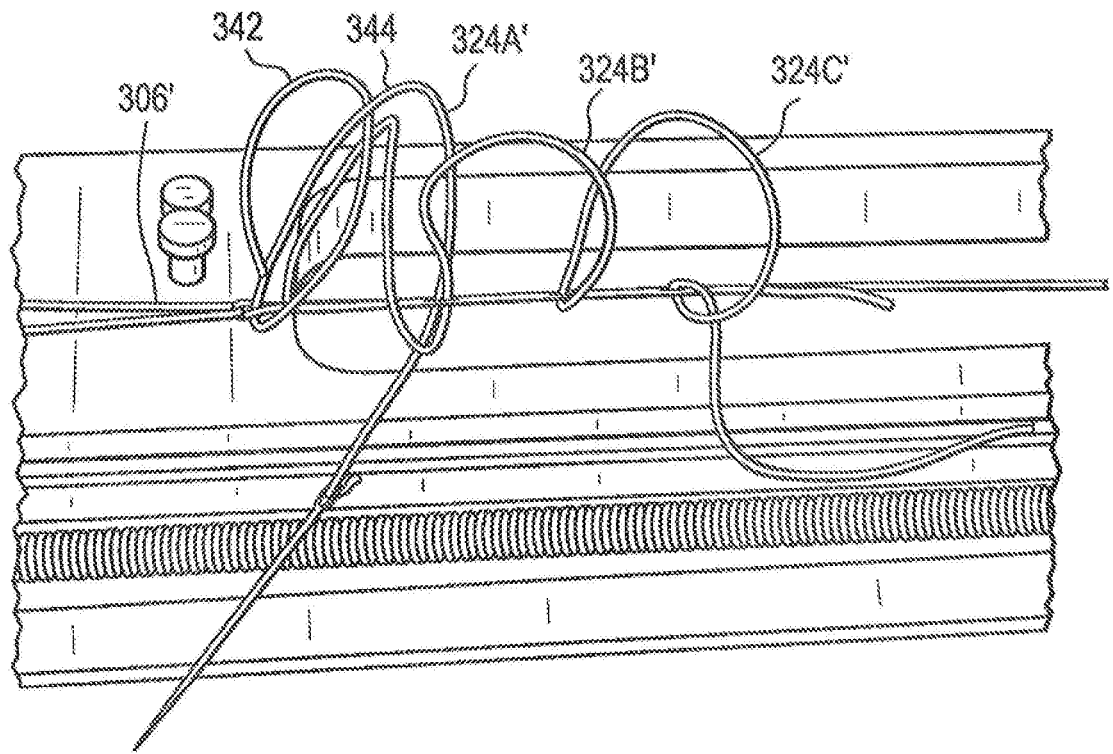
Figure 3M:
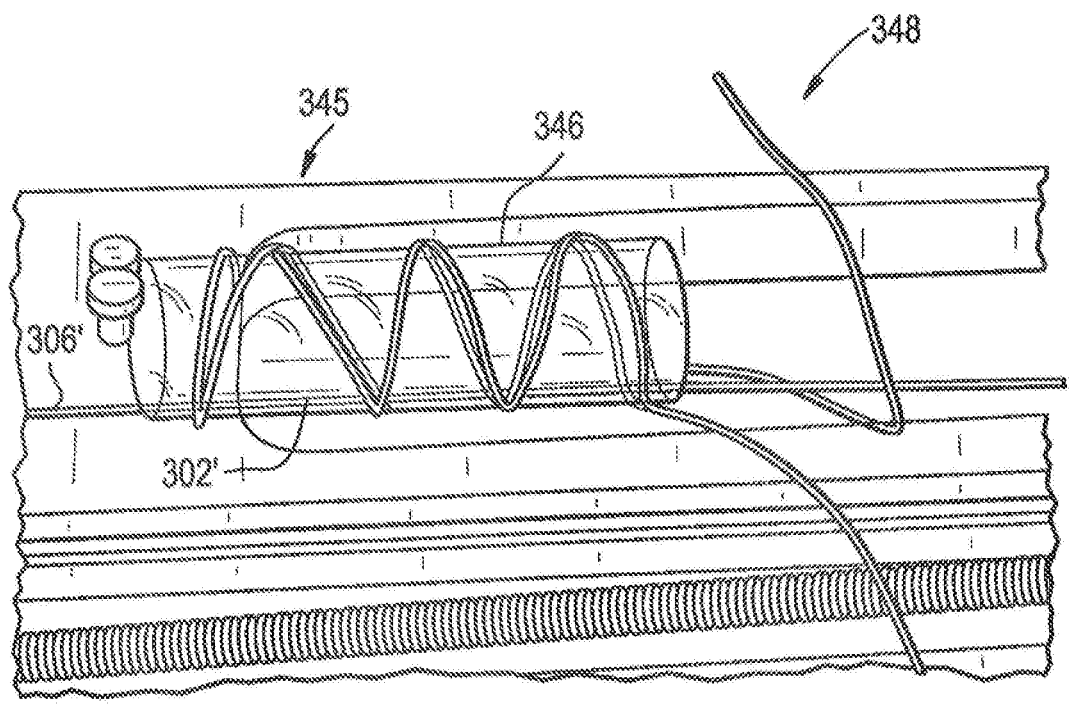

As shown in FIG. 3J, the suture 310' can next be brought around the spine 302' and passed through the eyelet 304' to thereby create a loop 342 (FIG. 3K) which can act as an end of the windings assembly (e.g., the loop forming the winding 210A in FIG. 2). The suture 310' can then be passed back in the opposite direction, towards the end 305B' of the spine 302', by being coupled with the spine 302' at a location 318A' as shown in FIG. 3L, to create a winding 344, and then at the locations 318B' and 318C,' each time creating a winding (not shown). The spine 302' having the windings collectively identified in FIG. 3M by a numerical reference 345 coupled thereto created as described above may then be positioned around a holder 346 (e.g., the elongate member 202 in FIG. 2 or any other holder) configured to deliver the assembly to a graft. A final assembly 348 shown in FIG. 3M can have the same structure as the assembly 204 in FIG. 2 made as shown in FIGS. 3A-3E. It should be appreciated, however, that the windings in accordance with some embodiments can be created in other suitable ways. Furthermore, in some embodiments, the delivery suture assembly may be deployed without using a holder.

Figure 4A:
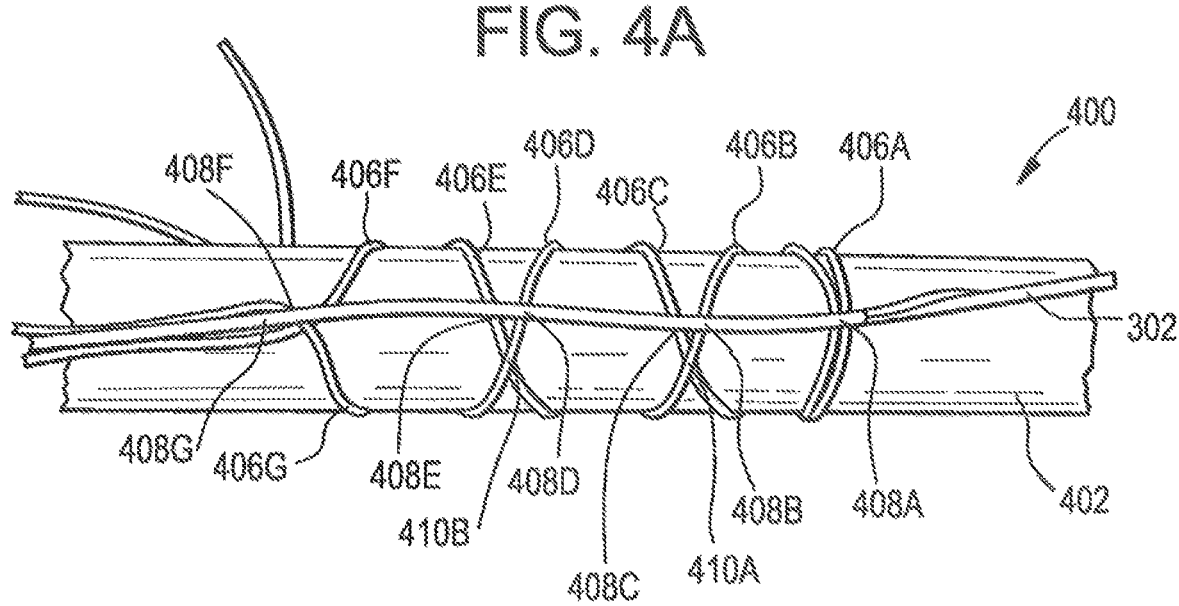
FIGS. 4A and 4B are alternative views of the graft preparation system in accordance with some embodiments.
Figure 4B:
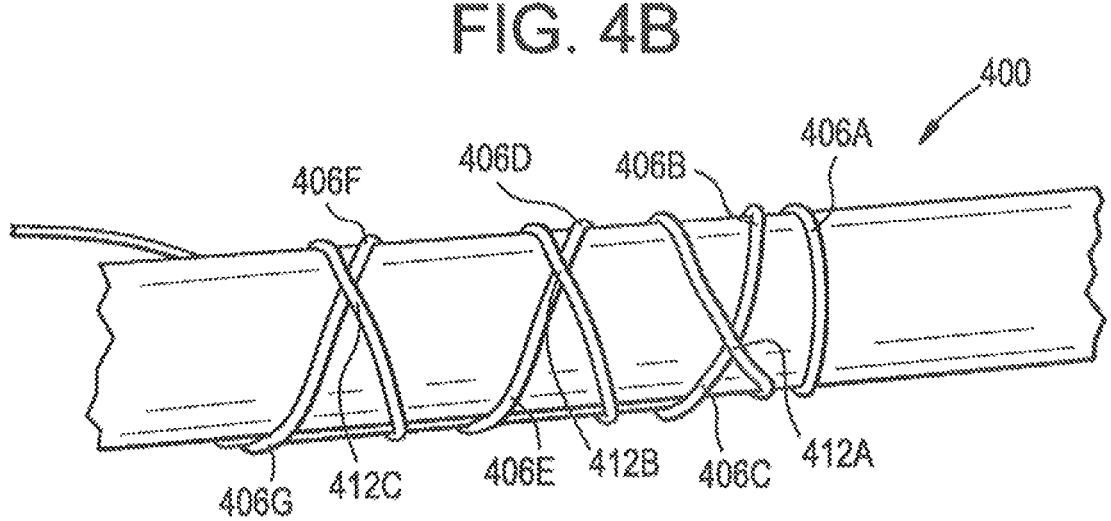

FIGS. 4A and 4B illustrate alternative views of a delivery suture assembly 400 formed in accordance with some embodiments, for example, as shown in connection with FIGS. 3A-3E. The delivery suture assembly 400 can be coupled to a holder 402 which, in the example illustrated, is an elongate holder which can have a changeable configuration capable of delivering the assembly 400 to a graft. For the sake of simplicity, the anchor suture 306 is not shown in FIGS. 4A and 4B, and only the windings formed from the suture 310 are illustrated.

In FIG. 4A, the assembly 400 is shown such that the spine 302 is visible. A plurality of windings 406A-406G formed from the suture 310 can be coupled with the spine 302 via attachment elements 408A-408G. The windings 406A-406G can be formed by loops, some of which are shown in FIG. 3E as loops 324A-324C. In this example, each of the windings 406A-406G is coupled with the spine 302 via a respective separate attachment element 408A-408G, one or more of which can be eyelets formed integrally with the spine. However, in some embodiments, the windings can be coupled to the spine via other types of attachment elements, including separate attachment elements.

As shown in FIG. 4A, the windings 406A-406G can form criss-crossing patterns 410A, 410B along an outer surface 403 of the holder 402. The windings formed in this way and coupled to the spine 302 allow distributing the load across the graft in a more uniform manner.

FIG. 4B illustrates an alternative view of the delivery suture assembly 400 where the spine 302 is not visible. FIG. 4B again shows that the 406A-406G can form criss-crossing patterns 412A-412C along an outer surface 403 of the holder 402.

Figure 5:
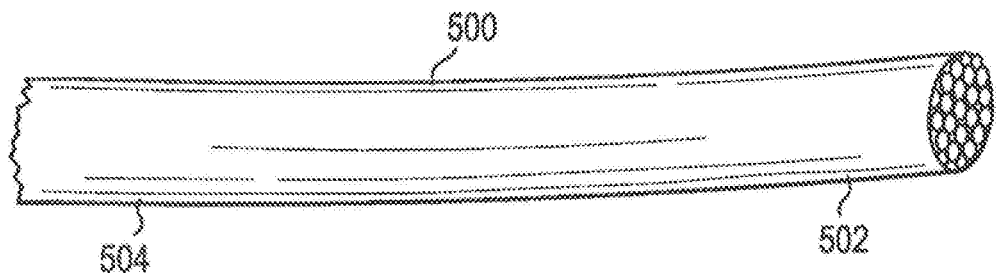
FIG. 5 is a schematic illustration of a graft.

FIG. 5 illustrates schematically a ligament graft 500 that can be prepared in accordance with some embodiments. The graft can be obtained either from the patient with the diseased or damaged ligament ("autograft") or from a donor ("allograft"). The graft 500 can include one or more tendon strands or other type of grafts. The graft 500 can be cleaned, sized and processed in other suitable ways prior to affixing sutures thereto in accordance with the described techniques.

As shown in FIG. 5, the graft 500 can have proximal and distal ends 502 and 504. As used herein, the "proximal" end can be defined as an end of the graft 500 that is nearest surgeon's hands preparing the graft 500. The "distal" end can be defined as an opposite end of the graft 500 which can be fixed using, for example, suitable graft preparation equipment. Alternatively, in some cases, the distal end 504 of the graft 500 can remain attached to the donor site of obtaining the graft 500 so that the graft 500 is prepared for the reconstruction surgery without being separated from that site.

FIGS. 6A-6E illustrate one embodiment of a method of delivering the graft preparation system 600 to the graft 500 and affixing suture(s) of the delivery suture assembly 204 onto the graft. These steps are also illustrated in FIGS. 7A-7H which are described below. In FIGS. 7A-7H, the graft 500 is shown as attached (e.g., clamped by jaws 702, without penetrating through the graft) at the distal end 504 thereof to a graft tensioning device 700. However, as mentioned above, in some embodiments, during the preparation of the graft 500 for a reconstruction surgery, the distal end 504 of the graft 500 can remain at the donor site from which the graft 500 is being harvested. Further, it should be appreciated that the delivery suture assembly is shown in FIGS. 7A-7H as being positioned at a middle portion of the graft for illustration purposes only, as the sutures may be affixed to an end portion of the graft.

Figure 6A:
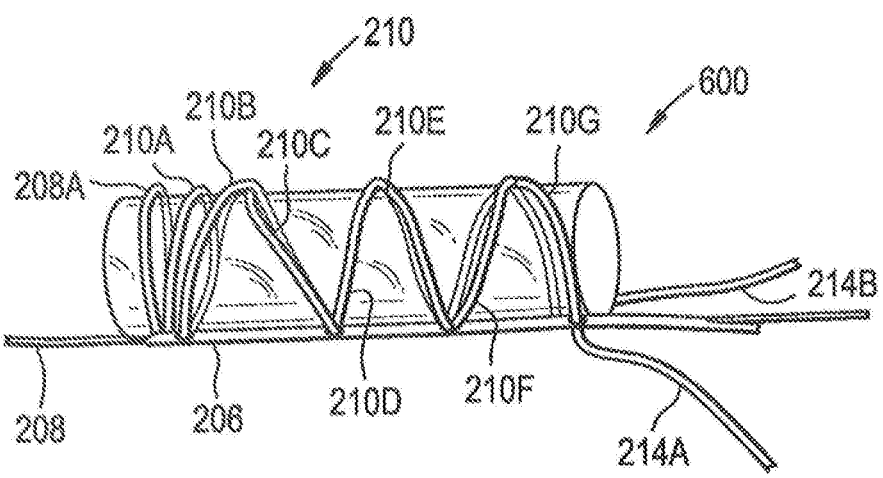
FIG. 6A is a schematic illustration of the graft preparation system in accordance with some embodiments.

FIG. 6A shows a graft preparation system 600 which is essentially identical to the graft preparation system 200 shown in FIG. 2, which is reproduced in FIG. 6A for clarity of representation. The graft preparation system 600 can have the same components as the graft preparation system 200, which are not described again to avoid repetition. In addition, not all of the components of the graft preparation system 200 are labeled in FIG. 6A.

Figure 7A:
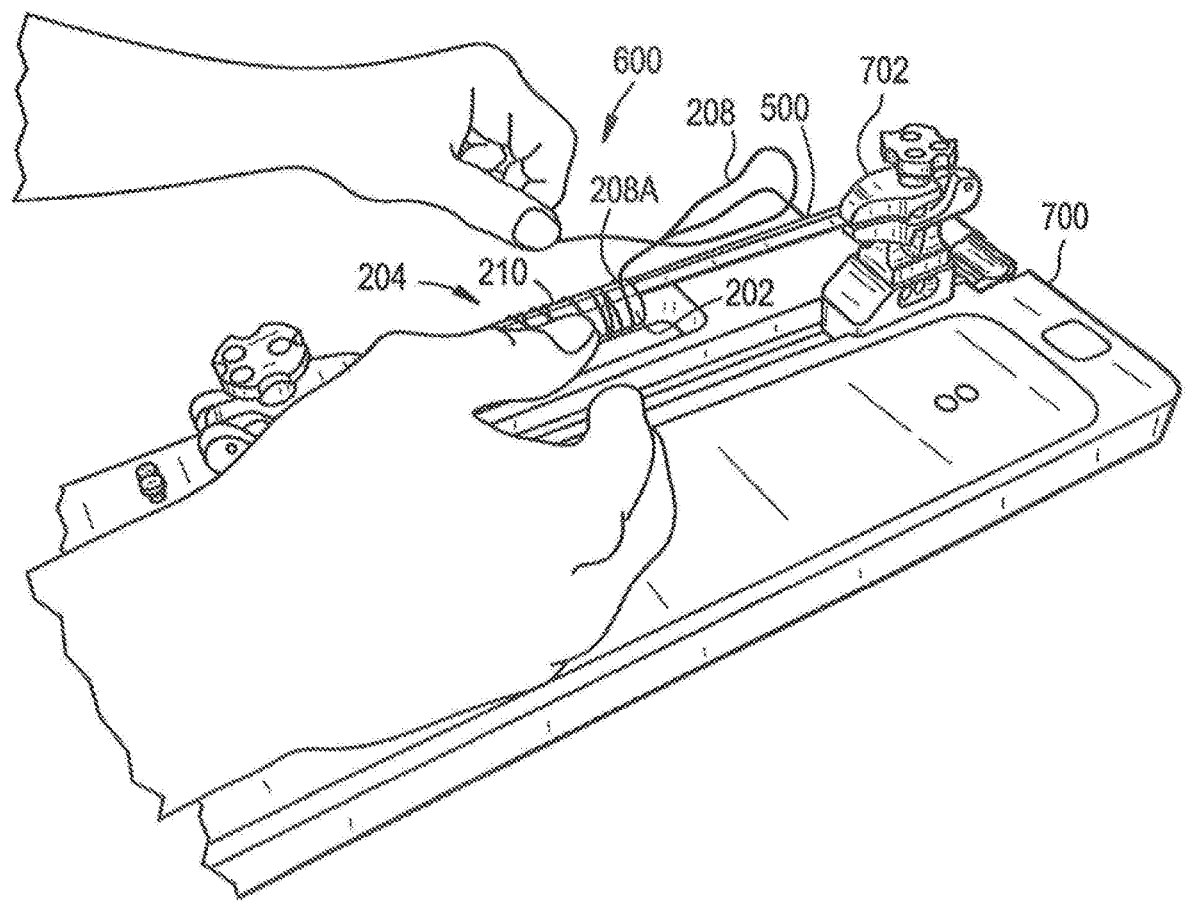
FIGS. 7A-7H are additional illustrations of steps of preparing a graft using a graft preparation system in accordance with some embodiments.

FIG. 7A illustrates another view of the graft 500 and the holder 202 positioned over the graft 500 and having the delivery suture assembly 204 removably associated therewith. In FIG. 7A, the holder 202 is held over the graft 500 such that the position of the holder 202 can be changed to determine an ultimate location at which the sutures are to be affixed to the graft 500.

Figure 6B:
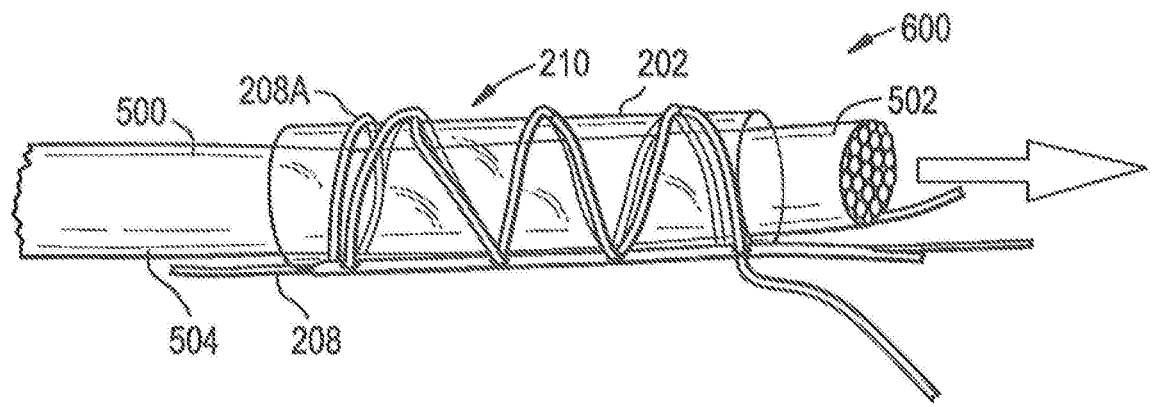
FIGS. 6B-6E are schematic illustrations of steps of preparing the graft of FIG. 5 using the graft preparation system of FIG. 6A.

As shown in FIG. 6B, the graft preparation system 600 can be positioned around a portion of the graft 500. The graft 500 can be received by the holder 202 in any suitable manner, which can depend from a configuration of the holder. For example, the graft 500 can be pushed through or pulled into the holder 202 or otherwise associated with the graft preparation system 600. The graft preparation system 600 can be positioned adjacent an end of the graft 500. In the example illustrated in FIGS. 6A-6E, the graft preparation system 600 is positioned over the graft 500 adjacent the proximal end 502 thereof. However, both ends of the graft 500 are typically prepared for the ligament reconstruction procedure. Accordingly, the end of the graft 500 being referred to as a proximal end when the sutures are being affixed thereto can be referred to as a distal end when the sutures are applied to the opposite end of the graft.

As mentioned above, the elongate holder 202 having a substantially cylindrical cross-section is shown herein by way of example only, as a holder having other suitable configurations can be used to carry a delivery suture assembly in accordance with the described techniques. Regardless of a type of the holder used, once the graft preparation system 600 is associated with the graft 500, the holder can be manipulated (e.g., to change a configuration thereof or otherwise manipulate it) such that the delivery suture assembly separates from the holder. In the example shown in FIG. 6C, the holder 202 is pulled out from under the snare 208A formed by the anchor suture 208 and the windings 210 in a direction shown by an arrow 602, towards the proximal end 502 of the graft 500.

Figure 7B:
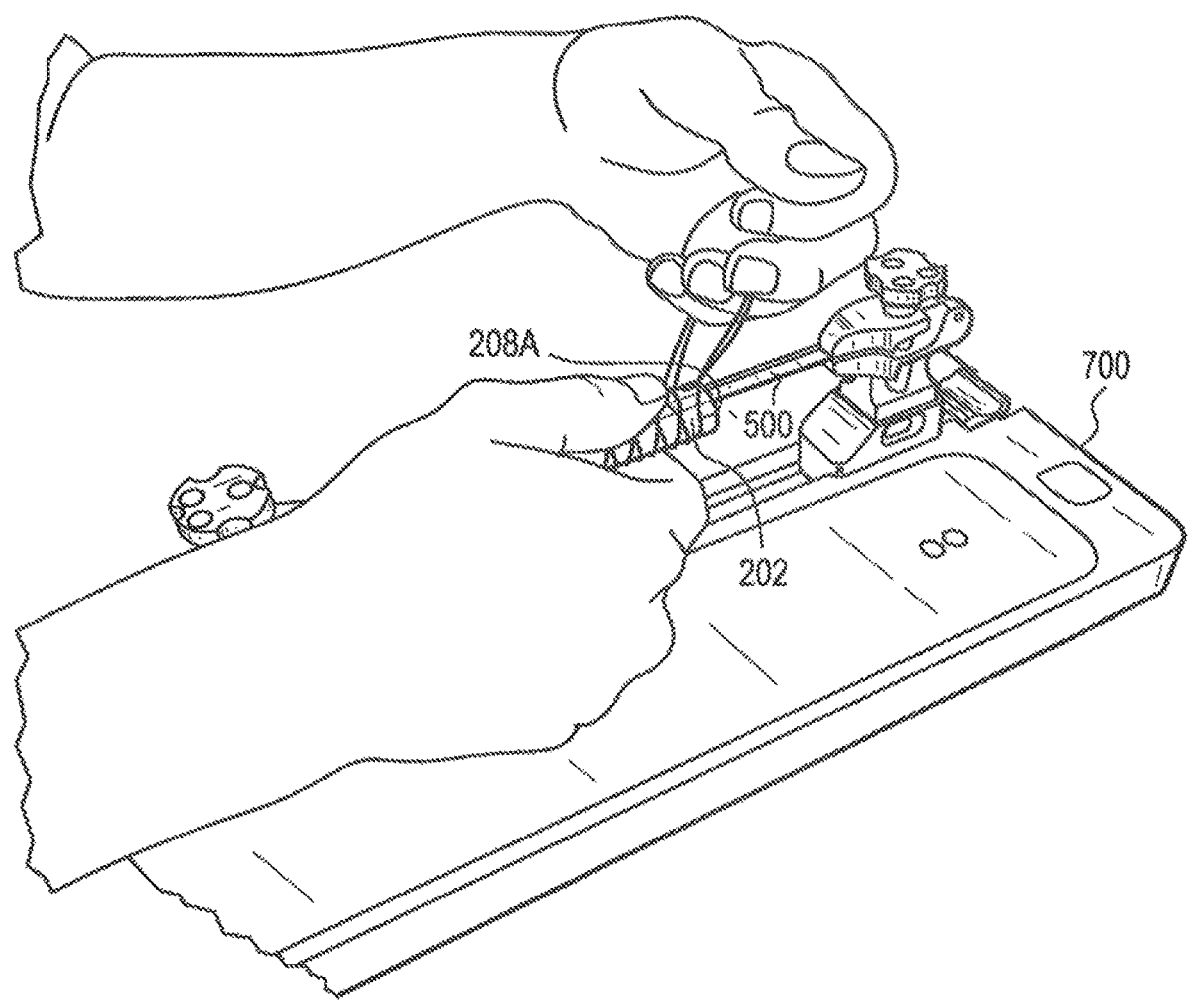
Figure 7C:
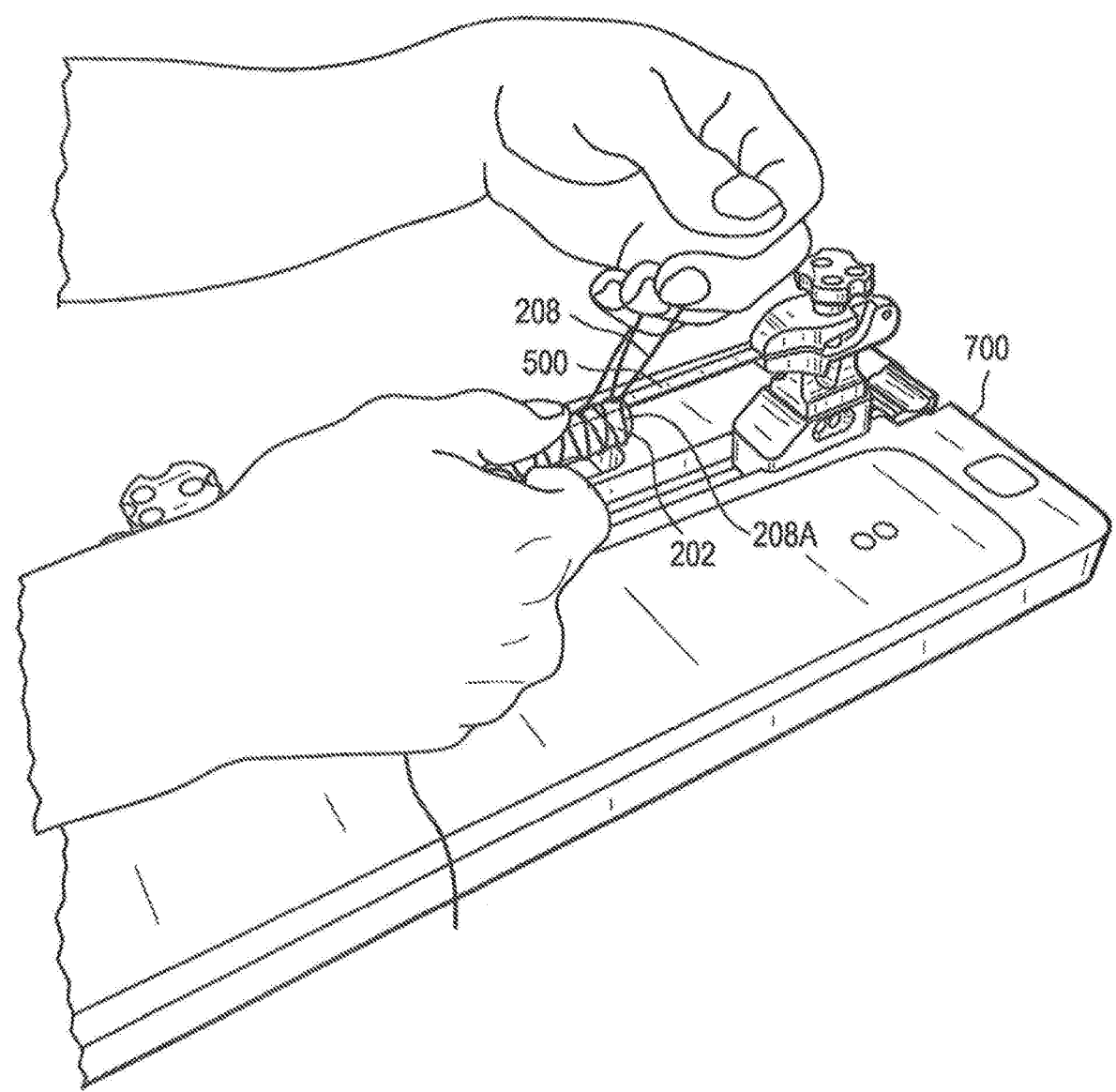
Figure 7D:
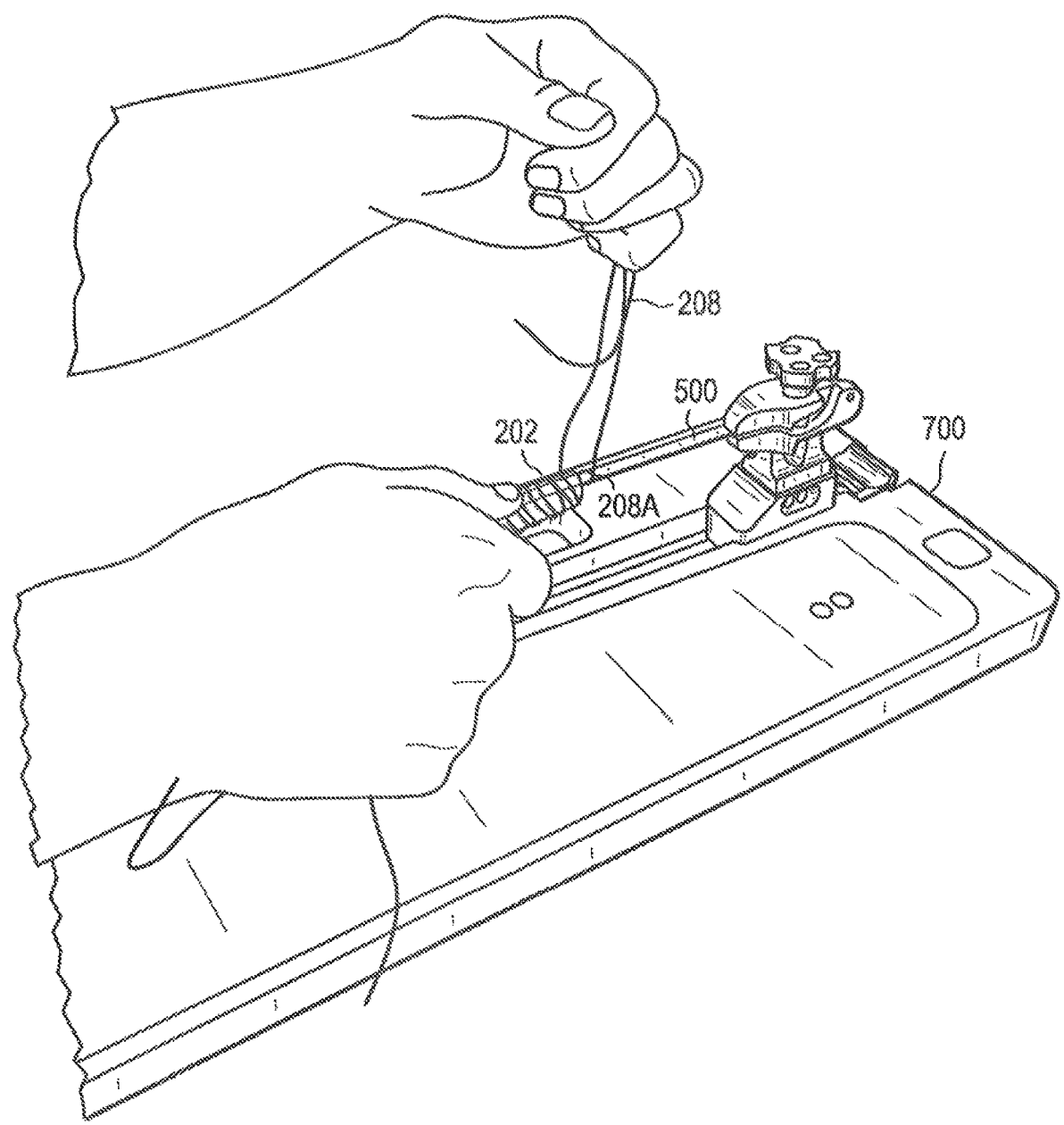

The holder 202 can have a configuration that allows one to manipulate the holder to change that configuration to thereby position the delivery suture assembly 204 around the graft 500. For example, the holder 202 can be made from a flexible material and can be pinched or otherwise deformed such that the delivery suture assembly 204 slides therefrom. FIGS. 7B-7D illustrate that the user can move the holder 202 while holding the anchor suture 208 to thereby separate the delivery suture assembly from the holder 202.

Figure 6C:
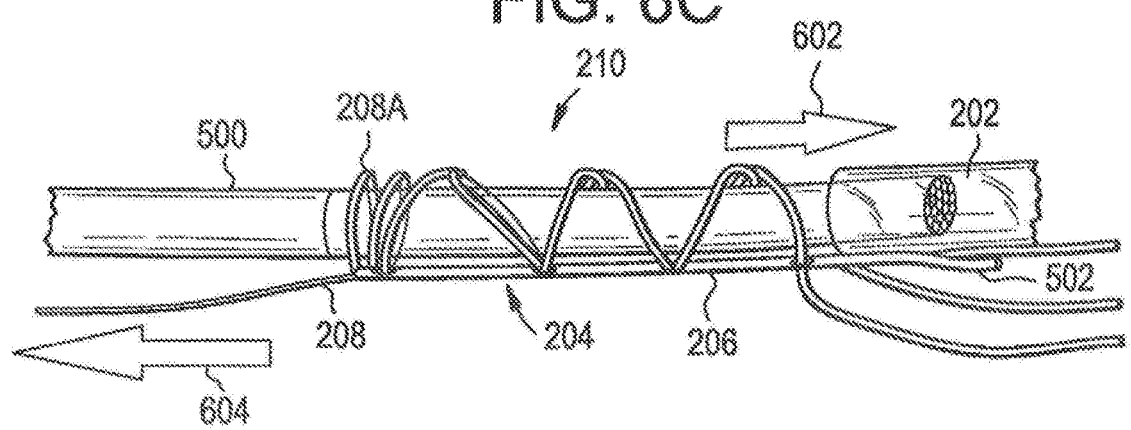
Figure 7E:
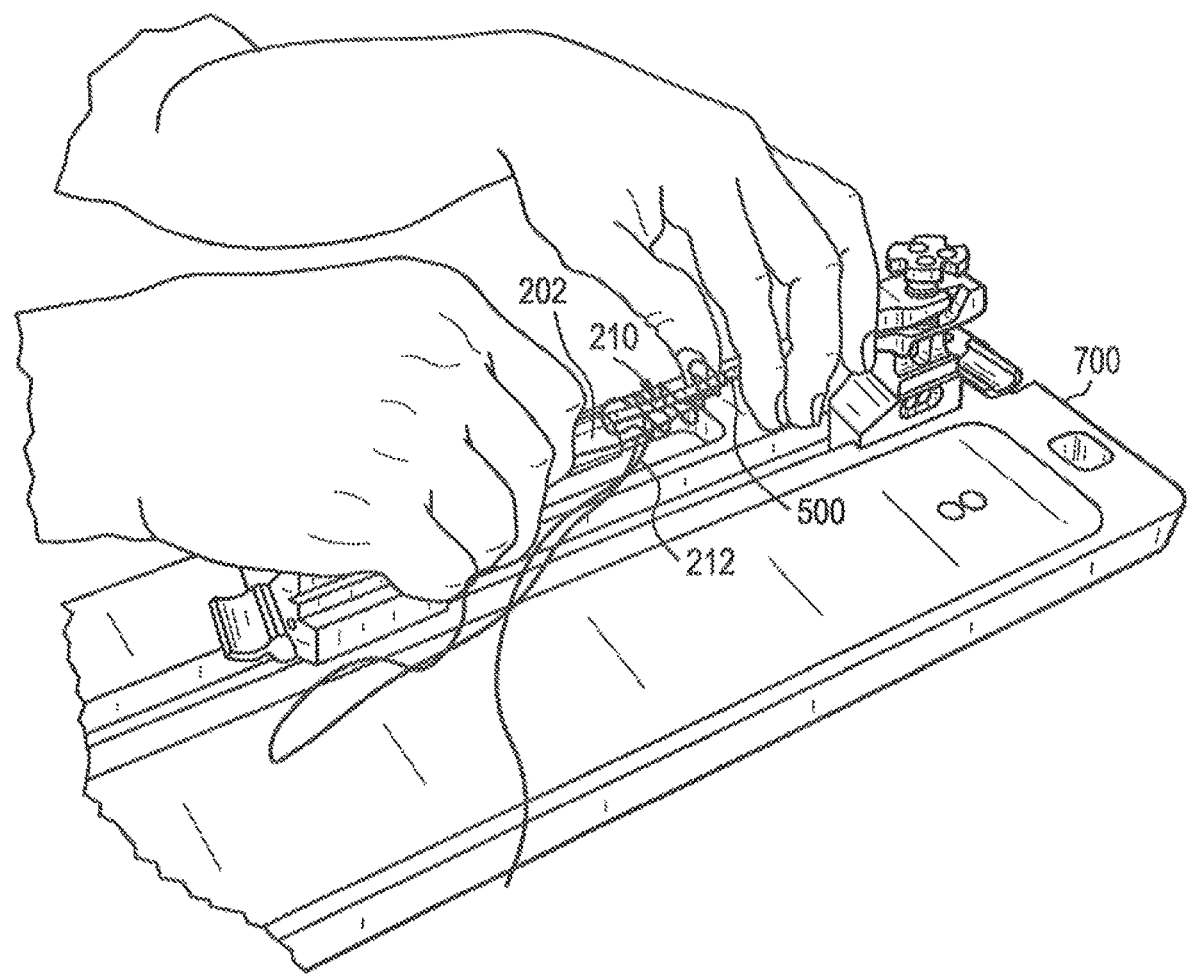

Accordingly, the holder 202 can be manipulated to be separated from the graft 500 whereas the delivery suture assembly 204 can remain positioned around the graft 500, as shown in FIG. 6C. As shown in FIG. 7E, after the holder 202 is withdrawn, the anchor suture 208 and windings 210 of the delivery suture assembly 204 remaining on the graft 500 can be loose loops positioned around the graft.

Figure 6D:
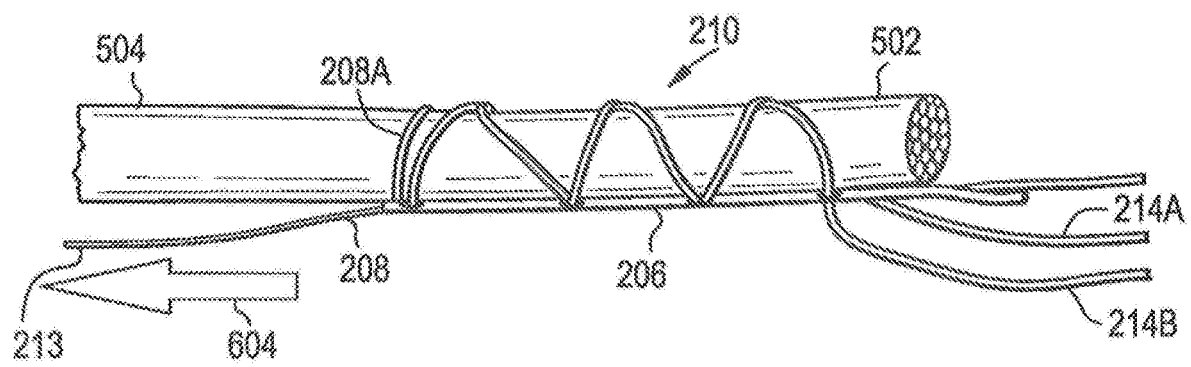

As illustrated in FIG. 6D, the tail 213 of the anchor suture 208 can be manipulated—e.g., pulled in a direction of an arrow 604 towards the distal end 504 of the graft 500 such that the pre-tied self-tightening snare 208A formed from the anchor suture 208 is tightened around the graft 500.

It should be appreciated that, in some embodiments, the anchor suture 208 can be separated from the holder 202 while at least a portion of the holder 202 is still associated with the graft 500 and at least some of the windings remain on the holder. In such embodiments, the tail 213 of the anchor suture 208 can be manipulated to affix the anchor suture 208 to the graft 500 prior to separating the delivery suture assembly 204 from the holder 202. As shown in FIG. 7B, the anchor suture 208 can be pulled away from the holder 202 to cause the self-tightening snare 208A to slide off the holder 202 as illustrated in FIG. 7C. This causes the snare 208A to self-tighten and to thereby become affixed around the graft 500, as shown in FIG. 7D where the snare 208A is positioned around the graft 500 while the holder 202 is held around the graft 500. The tightening of the snare 208A around the graft 500 anchors the location of the delivery suture assembly 204 on the graft 500.

Figure 7F:
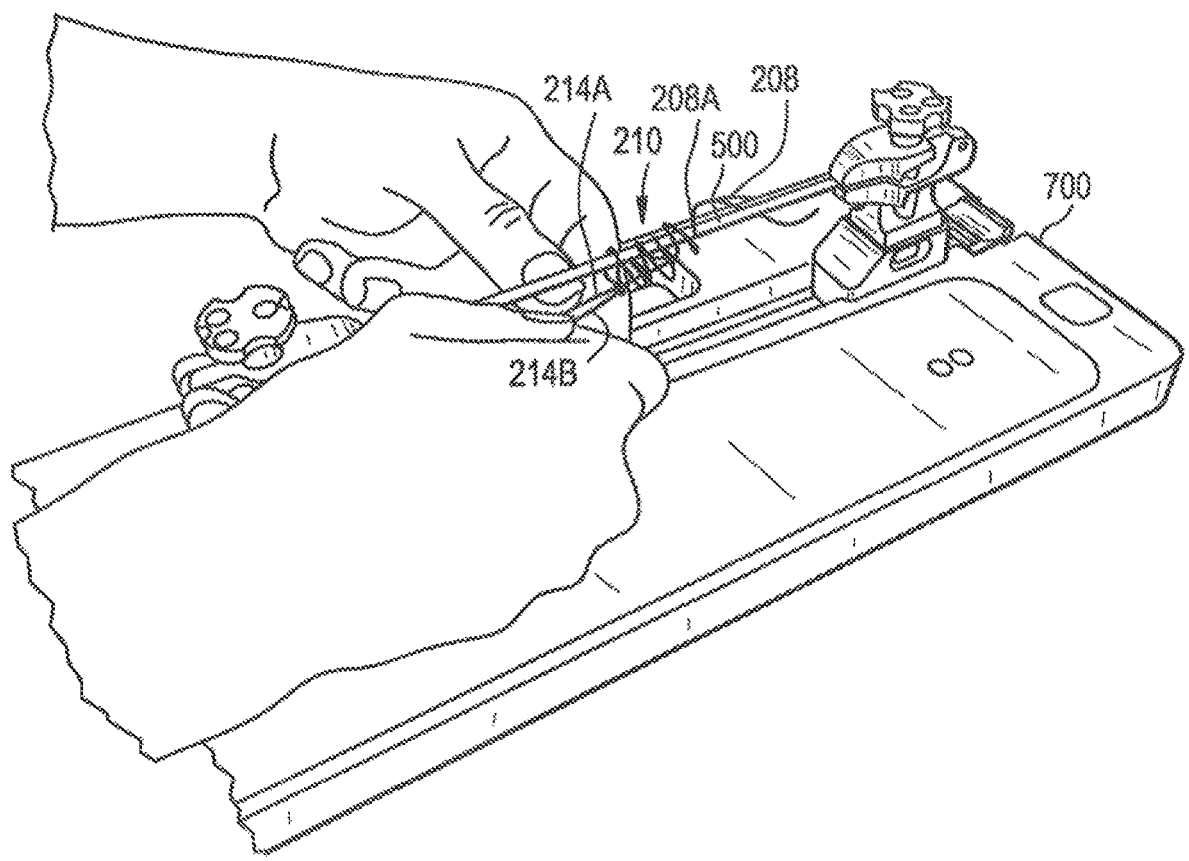

As shown in FIG. 7F, after the anchor suture 208 is used to position the delivery suture assembly 204 around the graft 500 using the snare 208A, the delivery suture assembly 204 can be separated from the holder 202. The windings 210 can form loose loops around the graft 500 after the holder 202 is removed, as shown in FIG. 7E.

Figure 6E:
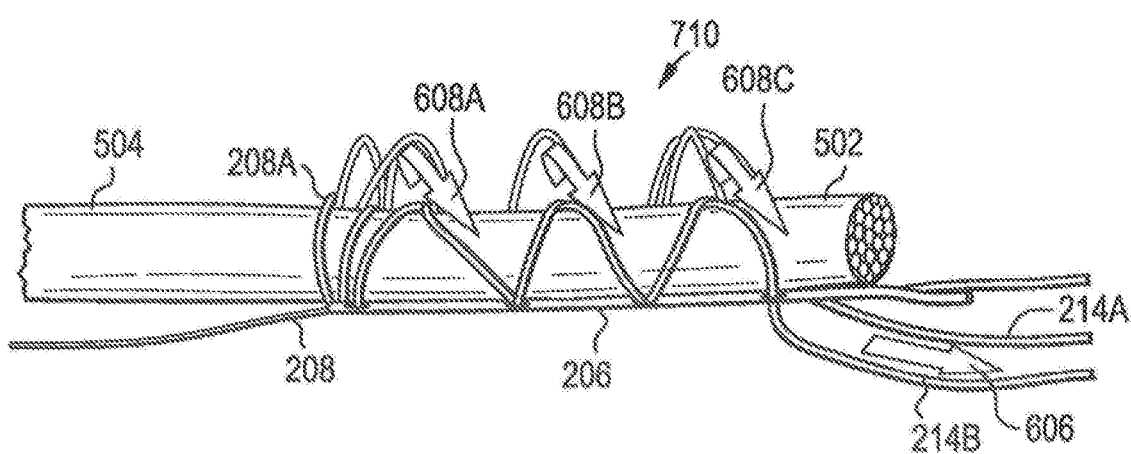
Figure 7G:
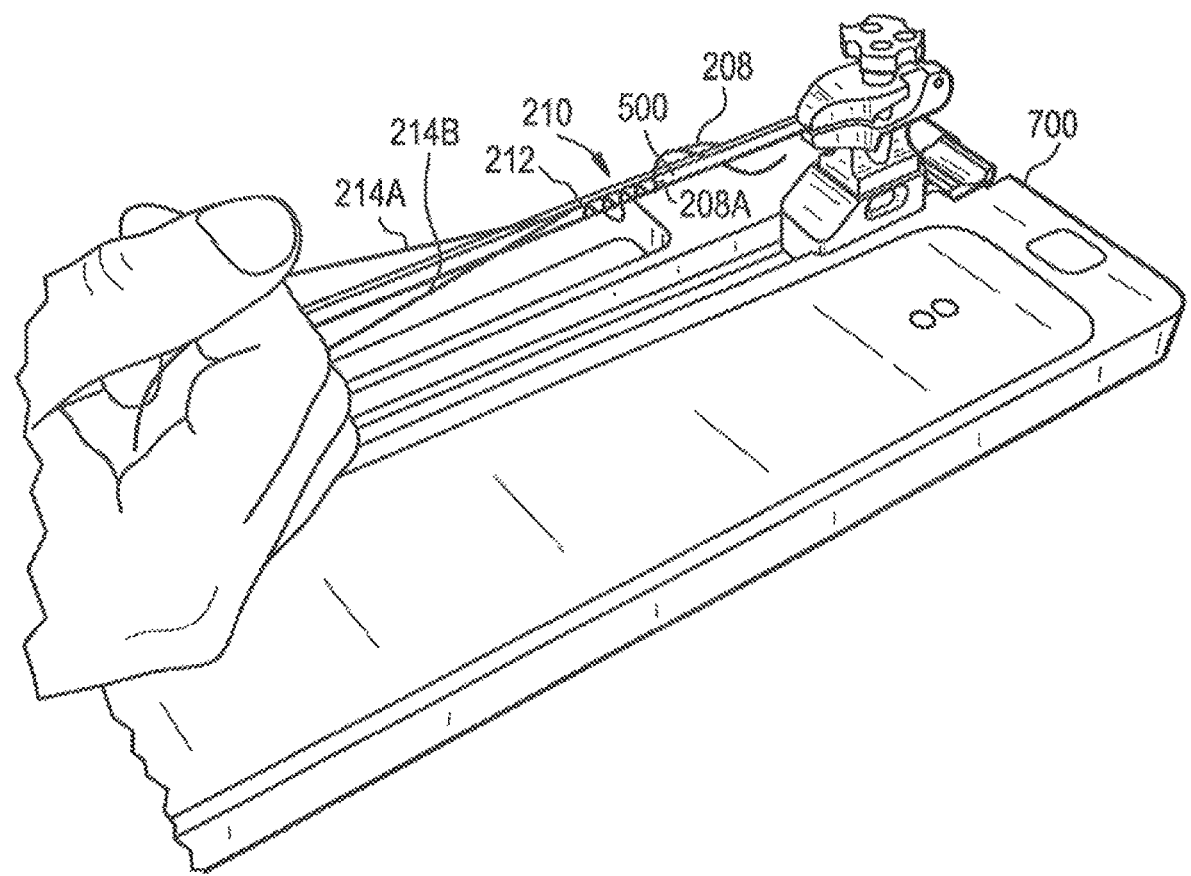

Next, after the self-tightening snare 208A is affixed around the graft 500 and the holder 202 is separated therefrom, the tails 214A, 214B of the windings 210 can be manipulated to tighten the loose loops thereof around the graft 500 as shown by arrows 608A-608C in FIG. 6E. For example, the tails 214A, 214B can be pulled in a direction of an arrow 606 which can be opposite to the direction of 604 at which the tail 213 of the anchor suture 208 was pulled. FIGS. 7F and 7G similarly illustrate that the tails 214A, 214B can be pulled to affix the suture 212 to the graft 500, with FIG. 7F illustrating a beginning of the process of manipulating the tails 214A, 214B when the windings 210 still form the loose loops around the graft. FIG. 7G illustrates a later stage of the process at which some of the windings 210 no longer form loose loops and instead are affixed to the graft 500 to compress the surface thereof.

The tails 214A and 214B can be pulled in an alternating fashion, such that the windings formed by the respective portions of the suture 212 are tightened in an alternating manner. However, the tails 214A, 214B can alternatively or additionally be pulled simultaneously, as embodiments are not limited to a specific way of manipulating the tails 214A, 214B to secure the windings 210 around the graft.

Figure 7H:
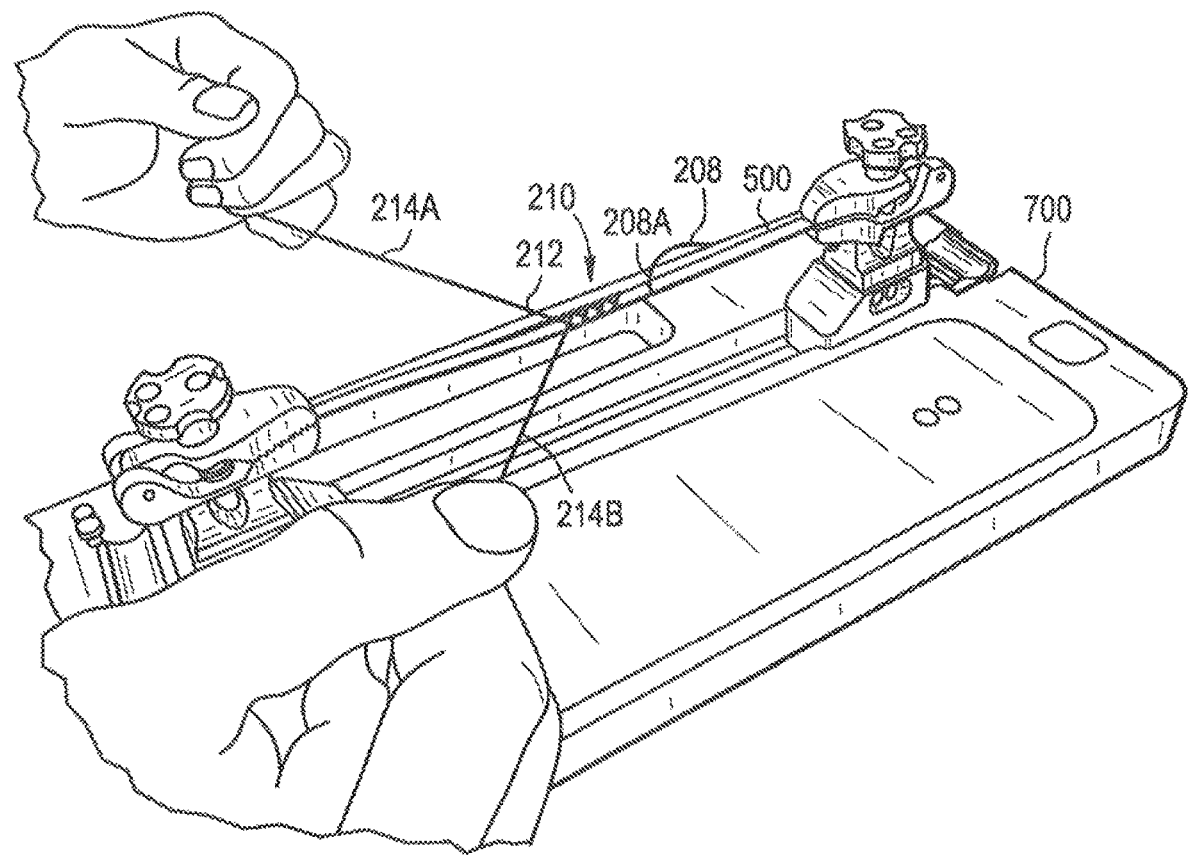

The tails 214A and 214B can be pulled while applying counter tension to the spine 206 which causes the windings 210 to cinch thereon and around the graft. The windings 210 can be secured around the graft such that they are evenly distributed around a portion of the graft and can thereby compress the graft with an approximately uniform force, which can prevent strangulation of the graft when the load is applied. The spine 206 can help to maintain appropriate spacing between the windings 210, which can increase contact of the suture 212 with the surface of the graft 500 and may ultimately improve the strength of fixation of the graft 500 to the reconstruction site. Furthermore, because of the more uniform distribution of the load among the windings, as compared to conventional approaches, elongation of the graft when the load is applied thereto can be decreased. In addition, the risk of graft fiber separation, pull-through or fraying of the graft can be reduced. FIG. 7H illustrates a final step of tightening the tails 214A, 214B to appropriately secure the windings 210 to the graft 500.

In some embodiments, after the windings 210 are affixed to the graft, the anchor suture 208 can be removed from the graft (e.g., cut off using an appropriate instrument). In some embodiments, alternatively or additionally, the spine 206 can be removed from the spine—for example, cut off using an appropriate instrument. However, in other embodiments, either or both the anchor suture and the spine can remain affixed to the graft when the graft is fixated in place (e.g., in the tunnels during the ACL reconstruction surgery).

Figure 8A:
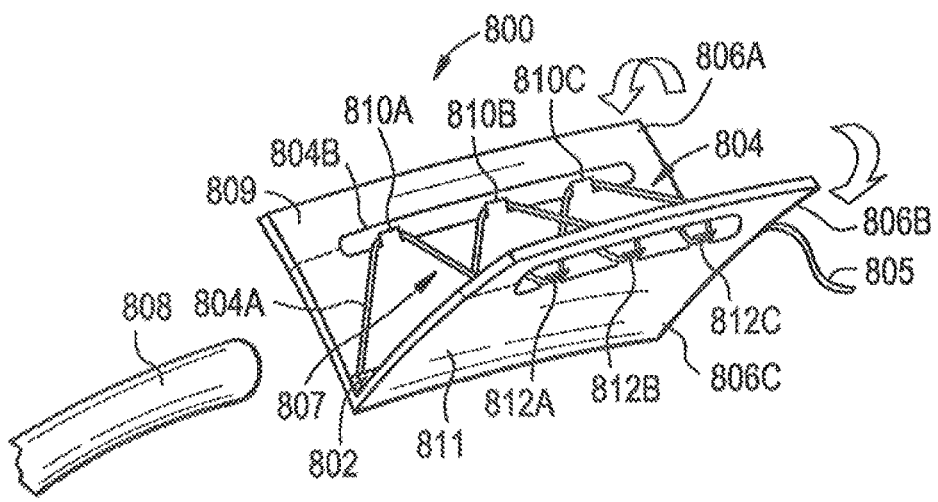
FIGS. 8A-8C are schematic illustrations of a graft preparation system including a card holder, in accordance with some embodiments.
Figure 8B:
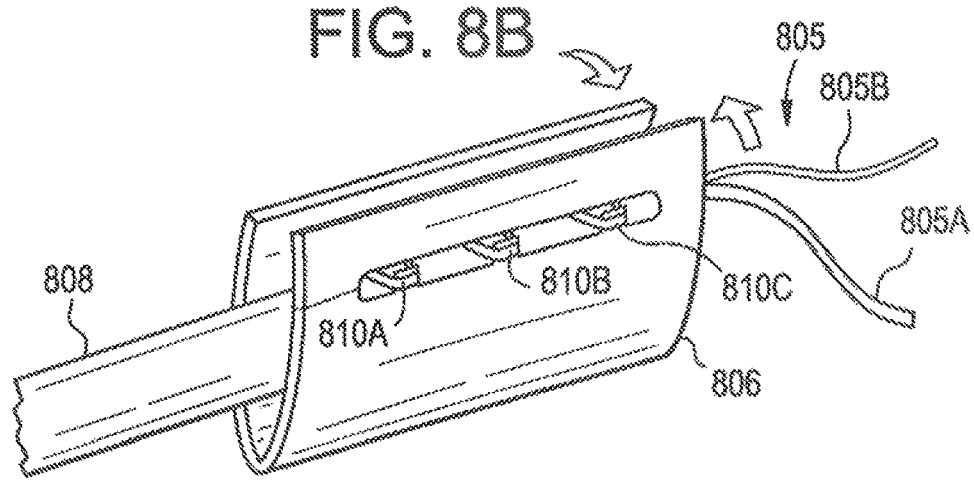
Figure 8C:
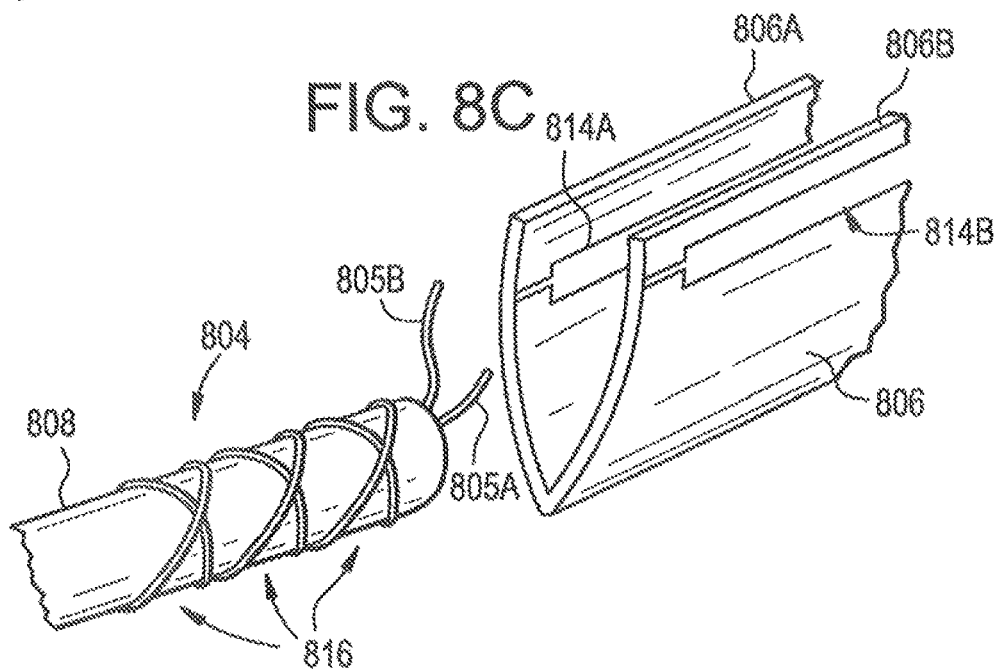

As discussed above, the described techniques may utilize any suitable type of a holder configured to deliver the delivery suture assembly to a graft. FIGS. 8A-8C illustrate an embodiment including a holder configured as a card-like structure having a generally rectangular configuration. As shown in FIG. 8A, a delivery suture assembly 800 can include a spine 802 and a plurality of windings 804 coupled thereto. The windings 804, which may be formed from a suture 805 or other type of material, can be coupled to the spine 802 in a variety of different ways. For example, each of the windings 804 may be coupled to the spine 802 or only some of the windings may be coupled to the spine 802. The portions of the windings 804 coupled to the spine 802 are labeled in FIG. 8A as elements 804A and 804B by way of example only. The spine 802 may be formed from a suture or from other (non-suture) type of material.

As shown in FIG. 8A, the spine 802 and the windings 804 can be coupled to a holder 806 configured to provide the delivery suture assembly 800 to a graft 808 schematically illustrated in FIG. 8A. The holder 806 may be a substantially rectangular element such that it is configured as a card having two portions 806A, 806B connected via a hinge portion 806C which can move from an open or partially open configuration (FIG. 8A) to a closed configuration (FIG. 8B) by pivoting the portions 806A, 806B around the hinge 806C (e.g., a fold). As used herein, a "substantially rectangular" can be defined as being generally formed as a rectangle (e.g., as viewed from a side) such that the opposite sides of the rectangle may not be exactly parallel or may not have the exact same length. Also, the corners of the element may be rounded off or shaped otherwise.

In this embodiment, the windings 804 can be coupled to the holder 806 such that a portion 807 of the windings 804 forming criss-crossing patterns is disposed on an inner surface 809 of the holder 806. The suture 805 forming the windings 804 can be coupled with the holder 806 by penetrating the holder 806 at locations 810A-810C (in the portion 806A) and 812A-812C (in the portion 806B) such that portions of the suture 805 are positioned on an outer surface 811 of the holder 806. It should be appreciated that three locations 810A-810C and 812A-812C at each of the portions 806A, 806B are shown as an example only, as the windings 804 can be coupled to the holder 806 in any other manner. For example, the holder 806 can have a suitable number of attachment elements for coupling the windings therewith. Furthermore, the holder 806 can have a configuration different from that shown in FIGS. 8A-8C.

The spine 802 can be coupled to the holder 806 by virtue of the suture 805 being coupled to the holder 806. Alternatively or additionally, the spine 802 can be coupled to the holder 806 in a suitable manner (e.g., using suitable attachment elements).

In use, as shown in FIG. 8B, the holder 806 can be positioned over the graft 808 such that the windings 804 (not visible in FIG. 8B) surround the graft 808. To position the delivery suture assembly 800 around the graft, the holder 806 can be moved from the open configuration (FIG. 8A) to a closed configuration (FIG. 8B). Tails 805A and 805B of the suture 805 are visible in FIG. 8B.

After it is positioned around the graft 808, the delivery suture assembly 800 can be separated from the holder 806 in a suitable manner. For example, the holder 806 can be made from a paper or other easily tearable material (such as a plastic film, for example) and the windings 804 can be separated from the holder 806 by tearing the holder 804 such that tears 814A, 814B can be formed in portions 806A, 806B of the holder 806. The holder 806 can then be removed, as shown in FIG. 8C. The windings 804 can be secured around the graft 808, for example, by manipulating the tails 805A and 805B of the suture 805, to thereby form criss-crossing patterns 816 around the graft 808 as shown in FIG. 8C. It should be appreciated that three criss-crossing patterns 816 are shown by way of example only, as any suitable number of windings configured to form any number of criss-crossing or other types of patterns can be utilized.

The delivery suture assembly 800 shown in FIGS. 8A-8B does not include an anchor suture. It should be appreciated, however, that the anchor suture or other element configured to position the spine 802 and the windings 804 coupled thereto on the graft may be included in the delivery suture assembly 800.

In some embodiments, a delivery suture assembly in accordance with some embodiments may be provided to a graft without the use of a separate holder. Such an embodiment is illustrated in FIG. 9 showing a delivery suture assembly 900 comprising a plurality of windings 902. The windings 902, which may be coupled to a spine (not shown), can be positioned around a grasper 904 or other surgical instrument that can be configured to grasp a graft 906 by jaws 908 or other members coupled to a distal end of a shaft 912 of the grasper 904. The windings 902 can be prepared such that, rather than forming loose loops, they are maintained in a stiffened, "open" configuration which may be achieved by coating the windings using a suitable material such as, for example, biocompatible coatings, wax of any suitable type, surgical glue or any other suitable material that can be used to stiffen the suture windings such that they maintain a configuration suitable for receiving a graft therethrough. The reinforced configuration of the windings and, in some embodiments, an anchor suture, may be temporary. For example, when the windings are positioned around the graft, their reinforced configuration may be changed to a more relaxed configuration such that the windings can be tightened and thereby secured around the graft.

The windings 902 can be slid over or otherwise positioned around the shaft 912 of the grasper 904 to be delivered to the graft 906. When the grasper 904 engages with the graft 906 (not shown), the windings 902 can be moved distally (i.e., away from a proximal end 911 of the shaft 912) to thereby be positioned around the graft 906. The windings 902 can then be secured around the graft 906, as discussed above.

As discussed above, in some embodiments, a holder used to deliver a delivery suture assembly to a graft may have a configuration different from that of a holder 202 shown, for example, in FIG. 2. FIGS. 10A-10C illustrate an embodiment where a holder has a reduced surface area.

As shown in FIG. 10A, a delivery suture assembly 1000 including windings 1002 may be positioned around a graft 1004 using a holder 1006. An anchor suture or a similar member may or may not be present.

The holder 1006 can include a holder spine 1008 and two end portions 1010 and 1012 formed at opposite ends of the holder spine 1008. As shown in FIGS. 10A and 10C, the end portions 1010 and 1012 can be arcuate and can circumscribe an arc in a range of about 180° to 360°. It should be appreciated, however, that the portions 1010, 1012 can have other shapes. Moreover, in some embodiments, the portions 1010, 1012 can be omitted.

As shown in FIGS. 10A and 10C, the holder spine 1008, positioned along an outer surface of the graft 1004, may have a relatively small thickness and it is configured to couple the windings 1002 with the holder 1006. Accordingly, in this embodiment, the holder spine 1008 can provide both the function of a suture spine (e.g., the spine 206 of FIG. 2)—to maintain the windings 1002 spaced apart from each other, and the function of delivering the windings 1002 to a graft in a ready-to-deploy configuration. In some embodiments, a suture spine can be used in conjunction with the holder 1006—for example, the suture spine can be disposed along a length of the holder spine 1008. In some cases, the suture spine can be omitted. The windings 1002 can be reinforced as described above to maintain a configuration suitable for receiving a graft therein.

As in the embodiments discussed above, when the delivery suture assembly 1000 is positioned around the graft 1004 using the holder 1006, the windings 1002 can be separated from the holder 1006 such that they remain positioned around the graft 1004. The windings 1002 can then be secured around the graft 1004, as schematically shown in FIG. 10B.

The holder 1006, which is shown in more detail in FIG. 10C, may include one or more attachment elements 1014A-1014D formed in the holder spine 1008. The attachment elements 1014A-1014D, which may be openings in the surface of the holder spine 1008 or other types of attachment elements, may be spaced longitudinally along a length of the holder spine 1008. To prepare the delivery suture assembly 1000, a suture 1003 forming the windings 1002 can be passed through the attachment elements 1014A-1014D to thereby couple the windings 1002 to the holder spine 1008.

As also shown in FIG. 10C, the holder 1006 may have other features that can maintain structural integrity of the holder and facilitate positioning of the delivery suture assembly 1000 around the graft. For example, the holder 1006 can include optional members 1016, 1018, in this example, each coupled with portions 1010 and 1012 as shown in FIG. 10C. The members 1016 and 1018 can assist in coupling the windings 1002 to the holder 1006 in a manner that can facilitate delivery of the windings 1002 (and, in some embodiments, an anchor suture or other similar element) to the graft. For example, the members 1016, 1018 can help maintain the loops forming the windings in an open configuration. As shown in FIG. 10C, each of the portions 1010 and 1012 can include one or more attachment elements such as the attachment elements 1020, 1022 and 1024, 1026 which can be used to pass the suture 1003 therethrough or to otherwise couple the suture 1003 with the holder 1006. Additionally or alternatively, an anchor suture can be passed through one or more of these attachment elements.

Although not shown in FIG. 10C, the members 1016, 1018 may have other features. For example, the holder 1006 can include more than two elements similar to the members 1016, 1018. Further, in some embodiments, the members 1016, 1018 may be omitted. The attachment elements 1020, 1022 and 1024, 1026 can be used to couple the sutures thereto or, in some cases, some or all of the attachment elements may be omitted as well.

The holder 1006, including optional members 1016, 1018, may be formed from a flexible material, such as plastic, fabric, metal foil, or any other suitable material. The holder 1006 may have a changeable configuration such that the configuration may be changed to deliver the delivery suture assembly 1000 to the graft. In addition, it should be appreciated that the holder 1006 described in connection with FIGS. 10A and 10C is by way of example only, as the described embodiments can employ a holder having any suitable configuration.

Figure 11:
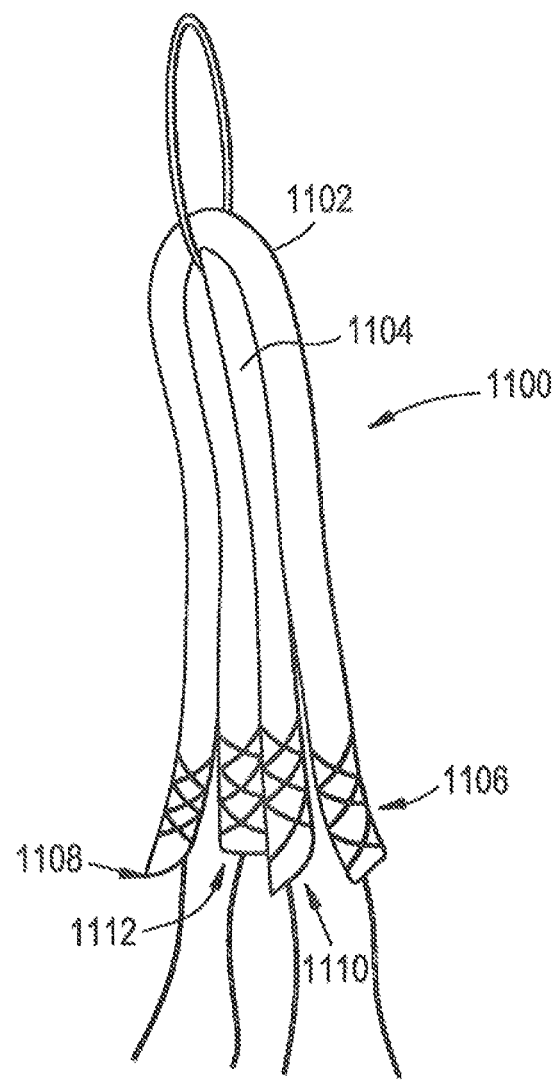
FIG. 11 is a schematic illustration of a graft prepared in accordance with some embodiments.

FIG. 11 illustrates a ligament graft 1100 prepared using the techniques described herein. In this example, two tendon strands 1102, 1104 may be used to replace a natural ligament. However, in some cases, grafts can be tripled or quadrupled to more closely replicate the structure of the natural ligament. It should be appreciated that any number of tendon strands or other types of graft can be used, as the embodiments described herein may be used for preparation of any types of grafts.

As shown in FIG. 11, both ends of each of the strands 1102, 1104 can be prepared by affixing sutures thereto in accordance with some embodiments. Thus, each of the strands 1102, 1104 has respective windings 1106, 1108 and 1110, 1112 affixed thereto. Anchor sutures are not shown in FIG. 11; however, it should be appreciated that, in some embodiments, the anchor sutures may be present on a prepared graft. The resulting graft 1100 is prepared without penetrating therethrough, which reduces a risk of damage of the graft during the reconstruction surgery. Furthermore, as described above, the graft 1100 can be prepared in an efficient and simple manner which can eliminate delays resulting from affixing sutures to grafts using conventional approaches.

Figure 12:
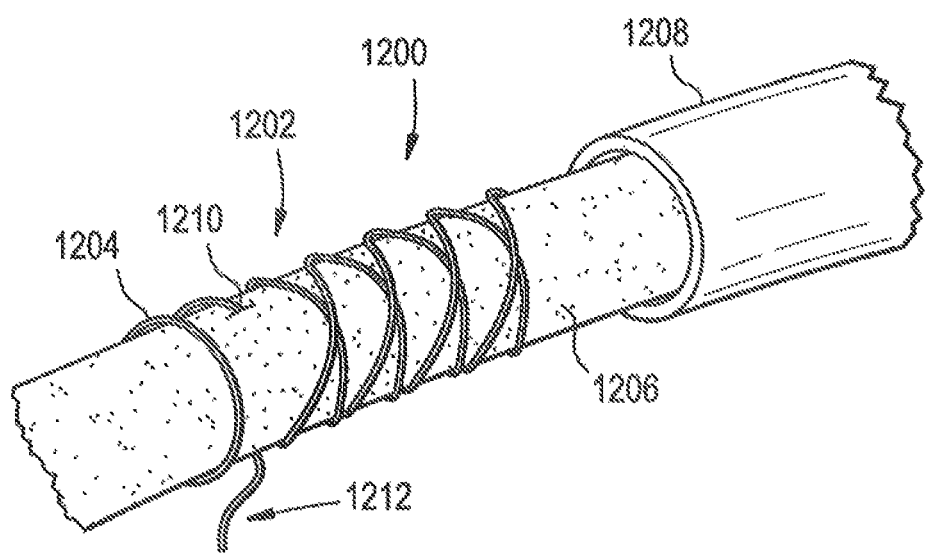
FIG. 12 is a schematic illustration of a graft preparation system including an anchoring element that can penetrate through a graft, in accordance with some embodiments.

In some embodiments, an anchor suture configured to lock a position of a delivery suture assembly around a graft may penetrate the graft for additional strength of attachment. FIG. 12 illustrates such an embodiment where a delivery suture assembly 1200 may include a plurality windings collectively referred to as windings 1202 and an anchoring element 1204 positioned around a graft 1206. In this example, the delivery suture assembly 1200 has been separated from a holder 1208.

As shown in FIG. 12, the anchoring element 1204 (e.g., a suture or other element(s)) may penetrate the graft 1206 at a location 1210 and a tail 1212 of the suture 1204 is shown in the opposite side of the graft 1206. It should be appreciated that the anchoring element 1204 may be passed through the graft 1206 in more than one location on the graft 1206. Also, additional loops, stitches or other techniques, not shown in FIG. 12, may be used to affix the anchoring element 1204 to the graft 1206 to thereby help to secure the windings 1202 at a particular location around the graft 1206.

It should be appreciated that although illustrated embodiments provide techniques for preparing anterior or posterior cruciate ligaments for ligament reconstruction surgery, the techniques can be adapted for preparation of other ligaments as well.

What is claimed is:

1. A method of preparing a graft for a surgical procedure, comprising:
   positioning a delivery suture assembly around a portion of the graft, the delivery suture assembly comprising a spine having first and second ends, a plurality of windings that are formed from a first suture and spaced longitudinally along the spine such that the windings are coupled to the spine by passing the first suture through attachment elements longitudinally spaced along the spine, wherein each of the plurality of windings is configured to be positioned entirely around the portion of the graft without penetrating the graft; and
   pulling at least one suture tail of the windings to secure the plurality of windings around the portion of the graft without penetrating the graft such that the windings are spaced apart along a length of the portion of the graft.

2. The method of claim 1, wherein the delivery suture assembly is positioned around the portion of the graft using a holder member having the delivery suture assembly removably associated therewith.

3. The method of claim 2, further comprising separating the delivery suture assembly positioned around the portion of the graft from the holder member such that the delivery suture assembly remains positioned around the portion of the graft and the holder member is removed.

4. The method of claim 3, wherein separating the delivery suture assembly from the holder member comprises changing a configuration of the holder member.

5. The method of claim 1, wherein at least one of the attachment elements comprises an eyelet formed in the spine.

6. The method of claim 5, wherein the eyelet is formed integrally with the spine.

7. The method of claim 1, wherein windings from the plurality of windings form a criss-crossing pattern.

* * * * *